United States Patent
Peyser

(10) Patent No.: US 7,691,608 B2
(45) Date of Patent: Apr. 6, 2010

(54) NUCLEIC ACIDS ENCODING RECOMBINANT PROTEIN A

(75) Inventor: James Ronald Peyser, Billerica, MA (US)

(73) Assignee: Repligen Corporation, Waltham, MA (US)

( * ) Notice: Subject to any disclaimer, the term of this patent is extended or adjusted under 35 U.S.C. 154(b) by 180 days.

(21) Appl. No.: 11/952,082

(22) Filed: Dec. 6, 2007

(65) Prior Publication Data

US 2009/0093017 A1 Apr. 9, 2009

Related U.S. Application Data

(60) Provisional application No. 60/873,191, filed on Dec. 6, 2006.

(51) Int. Cl.
C12P 21/06 (2006.01)
C12N 1/20 (2006.01)
C07H 21/04 (2006.01)

(52) U.S. Cl. .............. 435/69.1; 435/252.33; 435/320.1; 530/350; 530/412; 536/23.1

(58) Field of Classification Search .................. None
See application file for complete search history.

(56) References Cited

U.S. PATENT DOCUMENTS

| | | | |
|---|---|---|---|
| 3,549,524 A | 12/1970 | Haller | |
| 3,758,284 A | 9/1973 | Haller | |
| 3,850,798 A | 11/1974 | Sjöquist | |
| 3,983,000 A | 9/1976 | Messing et al. | |
| 3,995,018 A | 11/1976 | Sjöquist | |
| 4,681,870 A | 7/1987 | Balint et al. | |
| 5,084,559 A | 1/1992 | Profy | |
| 5,089,605 A * | 2/1992 | Profy et al. | 530/388.1 |
| 5,100,788 A | 3/1992 | Lofdahl et al. | |
| 5,143,844 A | 9/1992 | Abrahmsen et al. | |
| 5,151,350 A | 9/1992 | Colbert et al. | |
| 5,260,373 A | 11/1993 | Profy et al. | |
| 5,512,169 A | 4/1996 | Williams | |
| 5,601,979 A | 2/1997 | Wong | |
| 5,958,736 A | 9/1999 | Ståhl et al. | |
| 6,013,763 A | 1/2000 | Braisted et al. | |
| 6,197,927 B1 | 3/2001 | Braisted et al. | |
| 6,261,497 B1 | 7/2001 | Wong et al. | |
| 6,447,777 B1 | 9/2002 | Terman et al. | |
| 7,163,686 B1 | 1/2007 | Silverman | |
| 7,211,258 B2 | 5/2007 | Mann | |
| 7,425,331 B2 | 9/2008 | Mann | |
| 2002/0177551 A1 | 11/2002 | Terman | |
| 2003/0087864 A1 | 5/2003 | Talbot et al. | |
| 2005/0106597 A1 | 5/2005 | Choi | |
| 2005/0143566 A1 | 6/2005 | Hober | |
| 2006/0194950 A1 | 8/2006 | Hober et al. | |
| 2006/0194955 A1 | 8/2006 | Hober et al. | |
| 2006/0205016 A1 | 9/2006 | Silverman | |
| 2007/0129285 A1 | 6/2007 | Mann | |

| | | |
|---|---|---|
| 2007/0243582 A1 | 10/2007 | Kosugi et al. |

FOREIGN PATENT DOCUMENTS

| | | |
|---|---|---|
| EP | 0 230 869 | 5/1987 |
| EP | 0 284 368 | 9/1988 |
| EP | 0 324 867 | 7/1989 |
| EP | 0 355 047 | 2/1990 |
| EP | 0 550 771 | 7/1993 |
| EP | 1 179 014 | 2/2002 |
| EP | 1 355 532 | 10/2003 |
| EP | 1 485 407 | 12/2004 |
| EP | 1 767 640 | 3/2007 |
| WO | WO 79/00256 | 5/1979 |
| WO | WO 84/00773 | 1/1984 |
| WO | WO 84/00774 | 1/1984 |
| WO | WO 84/03103 | 8/1984 |
| WO | WO 93/02107 | 2/1993 |
| WO | WO 00/63243 | 10/2000 |
| WO | WO 00/69457 | 11/2000 |
| WO | WO 03/080655 | 10/2003 |
| WO | WO 03/086317 | 10/2003 |
| WO | WO 2005/115102 | * 12/2005 |
| WO | WO 2006/004067 | 1/2006 |
| WO | WO 2006/031786 | 3/2006 |
| WO | WO 2007/071692 | 6/2007 |

OTHER PUBLICATIONS

Uhlen et al. Expression of the gene encoding protein A in *Staphylococcus areous* and coagulase-negative *Staphylococci*. J. Bacteriol. Aug. 1984, vol. 159, (2), pp. 713-719.*
Abrahmsén et al., "Secretion of heterologous gene products to the culture medium of *Escherichia coli*," Nucleic Acids Res., 14:7487-7500 (1986).
Amersham Biosciences, "Protein A," 18-1060-56 AB (2001).
Bae et al., "The YSIRK-G/S motif of *staphylococcal* protein A and its role in efficiency of signal peptide processing," J. Bacteriol., 185:2910-19 (2003).
Bendsten et al., "Improved prediction of signal peptides: SignalP 3.0.," J. Mol. Biol., 340:783-795 (2004).
Choi et al., "Efficient secretory production alkaline phosphatase by high cell density culture of recombinant *Escherichia coli* using the *Bacillus* sp. endoxylanase signal sequence," Appl. Microbiol. Biotechnol., 53:640-645 (2000).
Choi et al., "Secretory and extracellular production of recombinant proteins using *Escherichia coli*," Appl. Microbiol. Biotechnol., 64:625-635 (2004).
Firestein, "Rheumatoid arthritis," Scientific American Medicine 15.II. (2000).
Fu et al., "Cell death caused by hyper-expression of a secretory exoglucanase in *Escherichia coli*," Protein Expr. Purif., 42:67-77 (2005).
Genbank Accession No. J01786.1 (1993).
Georgiou et al., "Preparative expression of secreted proteins in bacteria: status report and further prospects," Curr. Opin. Biotechnol., 16:538-545 (2005).

(Continued)

*Primary Examiner*—Nashaat T Nashed
(74) *Attorney, Agent, or Firm*—Fish & Richardson P.C.

(57) ABSTRACT

Disclosed are new recombinant nucleic acids encoding protein A polypeptides and methods of using these nucleic acids.

21 Claims, 12 Drawing Sheets

OTHER PUBLICATIONS

Goward et al., "Expression and purification of a truncated recombinant *streptococcal* Protein G," Biochem. J., 267:171-177 (1990).

Gustafsson et al., "Condon bias and heterologous protein expression," Trends Biotechnol., 22:346-353 (2004).

Hellebust et al., "Interaction between heat shock protein DnaK and recombinant *staphylococcal* protein A," J. Bacteriol., 172:5030-34 (1990).

Iordanescu et al., "Two restriction and modification systems in *Staphylococcus aureus* NCTC8325," J. Gen. Microbiol., 96:277-281 (1976).

Jeong et al., "Secretory production of human granulocyte colony-stimulating factor in *Escherichia coli*," Protein Expr. Purif., 23:311-318 (2001).

Jobling et al., "Construction and characterization of versatile cloning vectors for efficient delivery of native foreign proteins to the periplasm of *Escherichia coli*," Plasmid, 38:158-173 (1997).

Lee et al., "Secretory production of *Arthrobacter* levan fructotransferase from recombinant *Escherichia coli*," FEMS Microbiol. Left., 195:127-132 (2001).

Lindmark et al., "Extracellular protein A from methicillin-resistant strain of *Staphylococcus aureus*," Eur. J. Biochem., 74:623-628 (1977).

Löfdahl et al., "Gene for *staphylococcal* protein A," Proc. Natl. Acad. Sci. USA, 80:697-701 (1983).

Miksch et al., "The *kil* gene of the ColE1 plasmid of *Escherichia coli* controlled by a growth-phase-dependent promoter mediates the secretion of a heterologous periplasmic protein during the stationary phase," Arch. Microbiol., 167:143-150 (1997).

Millipore, "ProSep® -vA High Capacity Chromatography Media," Lit. No. DS1013EN00 (2004).

Miot et al., "Protein quality control in the bacterial periplasm," Microb. Cell Fact., 3:4 (2004) (13 pages).

Mirzabekov et al., "Enhanced expression, native purification, and characterization of CCR5, a principal HIV-1 coreceptor," J. Biol. Chem., 274:28745-50 (1999).

Movitz et al., "Physico- and immunochemical properties of *staphylococcal* protein A extracellularly produced by a set of mutants from *Staphylococcus aureus* Cowan I," Microbiol. Immunol., 23:51-60 (1979).

Movitz, "Formation of extracellular protein A by *Staphylococcus aureus*," Eur. J. Biochem., 68:291-299 (1976).

Nguyen et al., "*Staphylococcus aureus* protein A recognizes platelet gClqR/p33: a novel mechanism for *staphylococcal* interactions with platelets," Infect. Immun., 68:2061-68 (2000).

Nielson et al., "Prediction of signal peptides and signal anchors by a hidden Markov model," Proc. Int. Conf. Intell. Syst. Mol. Biol., 6:122-130 (1998).

Patel et al., "Regulation of the protein A-encoding gene in *Staphylococcus aureus*," Gene, 114:25-34 (1992).

Pratap et al., "Effect of signal peptide changes on the extracellular processing of *streptokinase* from *Escherichia coli*: requirement for secondary structure at the cleavage junction," Mol. Gen. Genet., 258:326-333 (1998).

Reichert et al., "Monoclonal antibodies market," Nature Rev., 3:283-384.

Shokri et al., "Cell and process design for targeting of recombinant protein into the culture medium of *Escherichia coli*," Appl. Microbiol. Biotechnol., 60:654-664 (2003).

Soares et al., "Periplasmic expression of human growth hormone via plasmid vectors containing the $\lambda P_L$ promoter: use of HPLC for product quantification," Protein Eng., 16:1131-38 (2003).

Söhlemann et al., "Expression in *Escherichia coli* of the genes coding for reaction center subunits from *Rhodabacter sphaeroides*: wild type proteins and fusion proteins containing one or four truncated domains from *Staphylococcus aureus* protein A at the carboxy-terminus," Biochim. Biophys. Acta, 1089:103-112 (1991).

Stader et al., "Engineering *Escherichia coli* to secrete heterologous gene products," Methods Enzymol, 185:166-187 (1990).

Tokugawa et al., "A novel protein secretion factor from *Vibrio* species which operates in *Escherichia coli*," J. Biotechnol., 35:69-76 (1994).

Uhlén et al., "Complete sequence of the *staphylococcal* gene encoding protein A," J. Biol. Chem., 259:1695-1702 (1984).

Van Wely et al., "Translocation of proteins across the cell envelope of Gram-positive bacteria," FEMS Microbiol. Rev., 25:437-454 (2001).

Warnes et al., "The membrane binding C-terminus of protein A from *Staphylococcus aureus* affects its cellular localization and causes structural deformation when expressed in *Escherichia coli*," Curr. Microbiol., 26:337-344 (1993).

European Search Report for EP 07 87 3663, dated Oct. 21, 2009 (3 pages).

International Search Report and Written Opinion for International Application No. PCT/US07/86692, dated Feb. 6, 2009 (11 pages).

* cited by examiner

Protein A Precursor Domain Map

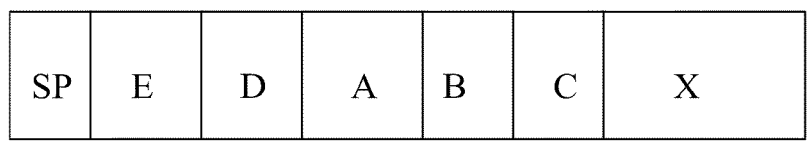

SP: Signal Peptide
E,D,A,B,C: IgG Binding Region
X: Anchoring Domain

Fig. 1

MKKKNIYSIRKLGVGIASVTLGTLLISGGVTPAANAAQHDEAQ
QNAFYQVLNMPNLNADQRNGFIQSLKDDPSQSANVLGEAQK
LNDSQAPKADAQQNNFNKDQQSAFYEILNMPNLNEAQRNGF
IQSLKDDPSQSTNVLGEAKKLNESQAPKADNNFNKEQQNAF
YEILNMPNLNEEQRNGFIQSLKDDPSQSANLLSEAKKLNESQ
APKADNKFNKEQQNAFYEILHLPNLNEEQRNGFIQSLKDDPS
QSANLLAEAKKLNDAQAPKADNKFNKEQQNAFYEILHLPNL
TEEQRNGFIQSLKDDPSVSKEILAEAKKLNDAQAPKEEDNNK
PGKEDNNKPGKEDNNKPGKEDNNKPGKEDNNKPGKEDNNK
PGKEDGNKPGKEDNKKPGKEDGNKPGKEDNKKPGKEDGN
KPGKEDGNKPGKEDGNGVHVVKPGDTVNDIAKANGTTADK
IAADNKLADKNMIKPGQELVVDKKQPANHADANKAQALPETG
EENPFIGTTVFGGLSLALGAALLAGRRREL (SEQ ID NO:4)

Fig. 2

E Domain
AQHDEAQQNAFYQVLNMPNLNADQRNGFIQSLKDDPSQSANVLGEAQKLNDSQA
PK (SEQ ID NO:9)

D domain
ADAQQNNFNKDQQSAFYEILNMPNLNEAQRNGFIQSLKDDPSQSTNVLGEAKKL
NESQAPK (SEQ ID NO:10)

A domain
ADNNFNKEQQNAFYEILNMPNLNEEQRNGFIQSLKDDPSQSANLLSEAKKLNES
QAPK (SEQ ID NO:11)

B domain
ADNKFNKEQQNAFYEILHLPNLNEEQRNGFIQSLKDDPSQSANLLAEAKKLNDA
QAPK (SEQ ID NO:12)

C domain
ADNKFNKEQQNAFYEILHLPNLTEEQRNGFIQSLKDDPSVSKEILAEAKKLNDA
QAPK (SEQ ID NO:13)

X domain 1
EEDNNKPGKEDNNKPGKEDNNKPGKEDNNKPGKEDNNKPGKEDNNKPGKEDGNK
PGKEDNKKPGKEDGNKPGKEDNKKPGKEDGNKPGKEDGNKPGKEDGNGVHVVKP
GDTVNDIAKANGTTADKIAADNKLADKNMIKPGQELVVDKKQPANHADANKAQA
LPETGEENPFIGTTVFGG (SEQ ID NO:14)

X domain 2
EEDNNKPGKEDNNKPGKEDNNKPGKEDNNKPGKEDNNKPGKEDNNKPGKEDGNK
PGKEDNKKPGKEDGNKPGKEDNKKPGKEDGNKPGKEDGNKPGKEDGNGVHVVKP
GDTVNDIAKANGTTADKIAADNK (SEQ ID NO:15)

Fig. 3

AQHDEAQQNAFYQVLNMPNLNADQRNGFIQSLKDDPSQSAN
VLGEAQKLNDSQAPKADAQQNNFNKDQQSAFYEILNMPNLN
EAQRNGFIQSLKDDPSQSTNVLGEAKKLNESQAPKADNNFN
KEQQNAFYEILNMPNLNEEQRNGFIQSLKDDPSQSANLLSE
AKKLNESQAPKADNKFNKEQQNAFYEILHLPNLNEEQRNGF
IQSLKDDPSQSANLLAEAKKLNDAQAPKADNKFNKEQQNAF
YEILHLPNLTEEQRNGFIQSLKDDPSVSKEILAEAKKLNDA
QAPKEEDNNKPGKEDNNKPGKEDNNKPGKEDNNKPGKEDNN
KPGKEDNNKPGKEDGNKPGKEDNKKPGKEDGNKPGKEDNKK
PGKEDGNKPGKEDGNKPGKEDGNGVHVVKPGDTVNDIAKAN
GTTADKIAADNKLADK (SEQ ID NO:7)

Fig. 4

MKKKNIYSIRKLGVGIASVTLGTLLISGGVTPAATAAQHDEAQQNA
FYQVLNMPNLNADQRNGFIQSLKDDPSQSANVLGEAQKLNDSQAPK
ADAQQNNFNKDQQSAFYEILNMPNLNEAQRNGFIQSLKDDPSQSTN
VLGEAKKLNESQAPKADNNFNKEQQNAFYEILNMPNLNEEQRNGFI
QSLKDDPSQSANLLSEAKKLNESQAPKADNKFNKEQQNAFYEILHL
PNLNEEQRNGFIQSLKDDPSQSANLLAEAKKLNDAQAPKADNKFNK
EQQNAFYEILHLPNLTEEQRNGFIQSLKDDPSVSKEILAEAKKLND
AQAPKEEDNNKPGKEDNNKPGKEDNNKPGKEDNNKPGKEDNNKPGK
EDNNKPGKEDGNKPGKEDNKKPGKEDGNKPGKEDNKKPGKEDGNKP
GKEDGNKPGKEDGNGVHVVKPGDTVNDIAKANGTTADKIAADNK
(SEQ ID NO:6)

Fig. 5 pREV2.1-rSPAv1 Sequence Landmarks

| | |
|---|---:|
| Origin of Replication (ORI) | 208-608 |
| β-glucuronidase promoter | 831-1039 |
| RBS | 1052-1056 |
| rSPAv1 (no signal sequence) | 1065-2336 |
| TrpA translational terminator | 2453-2480 |
| Chloramphenicol resistance | 3068-3727 |
| Ampicillin/Car

*GCAGCGGTCG GGCTGAACGG GGGGTTCGTG CACACAGCCC AGCTTGGAGC GAACGACCTA*
*CACCGAACTG AGATACCTAC AGCGTGAGCT ATGAGAAAGC GCCACGCTTC CCGAAGGGAG*
*AAAGGCGGAC AGGTATCCGG TAAGCGGCAG GGTCGGAACA GGAGAGCGCA CGAGGGAGCT*
*TCCAGGGGGA AACGCCTGGT ATCTTTATAG TCCTGTCGGG TTTCGCCACC TCTGACTTGA*
*GCGTCGATTT TTGTGATGCT CGTCAGGGGG GCGGAGCCTA TGGAAAAACG CCAGCAACGC*
*GGCCTTTTTA CGGTTCCTGG CCTTTTGCTG GCCTTTTGCT CACATGTTCT TTCCTGCGTT*
*ATCCCCTGAT TCTGTGGATA ACCGTATTAC CGCCTTTGAG TGAGCTGATA CCGCTCGCCG*
*CAGCCGAACG ACCGAGCGCA GCGAGTCAGT GAGCGAGGAA GCGGAAGAGC GCCTGATGCG*
*GTATTTTCTC CTTACGCATC TGTGCGGTAT TTCACACCGC* ATATGTCATG AGAGTTTATC
GTTCCCAATA CGCTCGAACG AACGTTCGGT TGCTTATTTT ATGGCTTCTG TCAACGCTGT
TTTAAAGATT AATGCGATCT ATATCACGCT GTGGGTATTG CAGTTTTTGG TTTTTTGATC
GCGGTGTCAG TTCTTTTTAT TTCCATTTCT CTTCCATGGG TTTCTCACAG ATAACTGTGT
GCAACACAGA ATTGGTTCGAACGCGTGGAGGATGATTAA
atggcgcaac acgatgaagc tcaacagaac gcttttacc aggtactgaa catgccgaac
ctgaacgcgg atcagcgcaa cggtttcatc cagagcctga agacgaccc ttctcagtcc
gcaaacgttc tgggcgaggc tcagaaactg aacgacagcc aggccccaaa agcagatgct
cagcaaaata acttcaacaa ggaccagcag agcgcattct acgaaatcct gaacatgcca
aatctgaacg aagctcaacg caacggcttc attcagtctc tgaaagacga tccgtcccag
tccactaacg ttctgggtga agctaagaag ctgaacgaat cccaggcacc aaaagcagac
aacaacttca acaaagagca gcagaacgct ttctatgaaa tcttgaacat gcctaacctg
aatgaagaac agcgtaacgg cttcatccag tctctgaagg acgaccctag ccagtctgct
aacctgctgt ccgaagcaaa aaaactgaac gagtcccagg ctccaaaagc ggataacaaa
ttcaacaagg agcagcagaa cgcattctac gaaatcctgc acctgccgaa cctgaacgaa
gaacagcgta acggtttcat ccaatccctg aagacgatc cttcccagtc cgcaaatctg
ctggcagaag caaagaaact gaacgacgca caggcaccga aggctgacaa caagttcaac
aaagagcagc agaatgcctt ctacgagatt ctgcatctgc caaacctgac tgaggagcag
cgcaacggtt tcattcagtc cctgaaggac gacccaagcg tcagcaagga atcctggct
gaggcgaaaa actgaacga tgcacaggct ccgaaggaag aagacaacaa taaacctggt
aaagaagata ataataagcc tggcaaggaa gataacaaca agccgggcaa ggaggacaac
aataaaccgg gcaaagagga taataacaag cctggtaagg aagacaacaa caaaccaggc
aaagaagatg gcaacaagcc gggtaaggag gataataaaa aaccaggcaa ggaagacggc
aacaaacctg gcaaggagga taacaaaaag ccaggcaagg aggatggtaa taaaccgggc
aaagaagacg gcaacaagcc tggtaaagaa gacggtaacg gtgtacacgt cgttaaacct
ggtgacaccg tgaacgacat cgctaaggct aatggcacca cggcagacaa gattgcagcg
gacaataaat aaGGATCCGG ATCCGTCGAC AAGCTTCCCG GGAGCTCGAA TTCTTGAAGA
*CGAAAGGGCC TCGTGATACG CCTATTTTTA TAGGTTAATG TCATGATAAT AATGGTTTCT*
*TAGACGTCGG TACCAGCCCG CCTAATGAGC GGGCTTTTTT TTGACGTCAG GTGGCACTTT*
*TCGGGGAAAT GTGCGCGGAA CCCCTATTTG TTTATTTTTC TAAATACAGA GGAAGACAAC*
*AACAAGCCTG G* (SEQ ID NO:16)

Fig. 7

```
ATGGCGCAAC ACGATGAAGC TCACCAGAAC GCTTTTTACC AGGTACTGAA
CATGCCGAAC CTGAACGCGG ATCAGCGCAA CGGTTTCATC CAGAGCCTGA
AGACGACCC TTCTCAGTCC GCAACGTTC TGGGCGAGGC TCAGAAACTG
AACGACAGCC AGGCCCCAAA AGCAGATGCT CAGCAAAATA ACTTCAACAA
GGACCAGCAG AGCGCATTCT ACGAAATCCT GAACATGCCA AATCTGAACG
AAGCTCAACG CAACGGCTTC ATTCAGTCTC TGAAAGACGA TCCGTCCCAG
TCCACTAACG TTCTGGGTGA AGCTAAGAAG CTGAACGAAT CCCAGGCACC
AAAAGCAGAC AACAACTTCA CAAAGAGCA GCAGAACGCT TTCTATGAAA
TCTTGAACAT GCCTAACCTG AATGAAGAAC AGCGTAACGG CTTCATCCAG
TCTCTGAAGG ACGACCCTAG CCAGTCTGCT AACCTGCTGT CCGAAGCAAA
AAAACTGAAC GAGTCCCAGG CTCCAAAAGC GGATAACAAA TTCAACAAGG
AGCAGCAGAA CGCATTCTAC GAAATCCTGC ACCTGCCGAA CCTGAACGAA
GAACAGCGTA ACGGTTTCAT CCAATCCCTG AAAGACGATC CTTCCCAGTC
CGCAAATCTG CTGGCAGAAG CAAAGAAACT GAACGACGCA CAGGCACCGA
AGGCTGACAA CAAGTTCAAC AAAGAGCAGC AGAATGCCTT CTACGAGATT
CTGCATCTGC CAAACCTGAC TGAGGAGCAG CGCAACGGTT TCATTCAGTC
CCTGAAGGAC GACCCAAGCG TCAGCAAGGA AATCCTGGCT GAGGCGAAAA
AACTGAACGA TGCACAGGCT CCGAAGGAAG AAGACAACAA TAAACCTGGT
AAAGAAGATA ATAATAAGCC TGGCAAGGAA GATAACAACA AGCCGGGCAA
GGAGGACAAC AATAAACCGG GCAAAGAGGA TAATAACAAG CCTGGTAAGG
AAGACAACAA CAAACCAGGC AAAGAAGATG CAACAAGCC GGGTAAGGAG
GATAATAAAA AACCAGGCAA GGAAGACGGC AACAAACCTG CAAGGAGGA
TAACAAAAAG CCAGGCAAGG AGGATGGTAA TAAACCGGGC AAAGAAGACG
GCAACAAGCC TGGTAAAGAA GACGGTAACG GTGTACACGT CGTTAAACCT
GGTGACACCG TGAACGACAT CGCTAAGGCT AATGGCACCA CGGCAGACAA
GATTGCAGCG ACAATAAAT TAGCTGATAA ATAAGGATCC GGATCCGTCG
ACAAGCTTCC CGGGAGCTCG AATTCTTGAA GACGAAGGG CCTCGTGATA
CGCCTATTTT TATAGGTTAA TGTCATGATA ATAATGGTTT CTTAGACGTC
GGTACCAGCC CGCCTAATGA GCGGGCTTTT TTTTGACGTC AGGTGGCACT
TTTCGGGGAA ATGTGCGCGG AACCCCTATT TGTTTATTTT TCTAAATACA
GAGGAAGACA ACAACAAGCC TGG  (SEQ ID NO:2)
```

Fig. 10

AQHDEAQQNAFYQVLNMPNLNADQRNGFIQSLKDDPSQSANVLGEAQKLNDS
QAPKADAQQNNFNKDQQSAFYEILNMPNLNEAQRNGFIQSLKDDPSQSTNVL
GEAKKLNESQAPKADNNFNKEQQNAFYEILNMPNLNEEQRNGFIQSLKDDPS
QSANLLSEAKKLNESQAPKADNKFNKEQQNAFYEILHLPNLNEEQRNGFIQS
LKDDPSQSANLLAEAKKLNDAQAPKADNKFNKEQQNAFYEILHLPNLTEEQR
NGFIQSLKDDPSVSKEILAEAKKLNDAQAPKEEDNNKPGKEDNNKPGKEDNN
KPGKEDNNKPGKEDNNKPGKEDNNKPGKEDGNKPGKEDNKKPGKEDGNKPGK
EDNKKPGKEDGNKPGKEDGNKPGKEDGNGVHVVKPGDTVNDIAKANGTTADK
IAADNKLADKNMIKPGQELVVDKKQPANHADANKAQALPETGEENPFIGTTV
FGG (SEQ ID NO:17)

Fig. 11

AQHDEAQQNAFYQVLNMPNLNADQRNGFIQSLKDDPSQSANVLGEAQKLNDS
QAPKADAQQNNFNKDQQSAFYEILNMPNLNEAQRNGFIQSLKDDPSQSTNVL
GEAKKLNESQAPKADNNFNKEQQNAFYEILNMPNLNEEQRNGFIQSLKDDPS
QSANLLSEAKKLNESQAPKADNKFNKEQQNAFYEILHLPNLNEEQRNGFIQS
LKDDPSQSANLLAEAKKLNDAQAPKADNKFNKEQQNAFYEILHLPNLTEEQR
NGFIQSLKDDPSVSKEILAEAKKLNDAQAPKEEDNNKPGKEDNNKPGKEDNN
KPGKEDNNKPGKEDNNKPGKEDNNKPGKEDGNKPGKEDNKKPGKEDGNKPGK
EDNKKPGKEDGNKPGKEDGNKPGKEDGNGVHVVKPGDTVNDIAKANGTTADK
IAADNK (SEQ ID NO:5)

Fig. 12

```
atggcgcaacacgatgaagctcaacaaaatgctttttatcaagtcttaaata
tgcctaacttaaatgctgatcaacgcaatggttttatccaaagccttaaaga
tgatccaagccaaagtgctaacgttttaggtgaagctcaaaaacttaatgac
tctcaagctccaaaagctgatgcgcaacaaaataacttcaacaaagatcaac
aaagcgccttctatgaaatcttgaacatgcctaacttaaacgaagcgcaacg
taacggcttcattcaaagtcttaaagacgacccaagccaaagcactaacgtt
ttaggtgaagctaaaaattaaacgaatctcaagcaccgaaagctgataaca
atttcaacaaagaacaacaaaatgctttctatgaaatcttgaatatgcctaa
cttaaacgaagaacaacgcaatggtttcatccaaagcttaaaagatgaccca
agccaaagtgctaacctattgtcagaagctaaaaagttaaatgaatctcaag
caccgaaagcggataacaaattcaacaaagaacaacaaaatgctttctatga
atcttacatttacctaacttaaacgaagaacaacgcaatggtttcatccaa
agcctaaaagatgacccaagccaaagcgctaacctttagcagaagctaaaa
agctaaatgatgctcaagcaccaaaagctgacaacaaattcaacaaagaaca
acaaaatgctttctatgaatttacatttacctaacttaactgaagaacaa
cgtaacggcttcatccaaagccttaaagacgatccttcggtgagcaaagaaa
ttttagcagaagctaaaaagctaaacgatgctcaagcaccaaaagaggaaga
caataacaagcctggcaaagaagacaataacaagcctggcaaagaagacaat
aacaagcctggcaaagaagacaacaacaagcctggcaaagaagacaacaaca
agcctggtaaagaagacaacaacaagcctggcaaagaagacggcaacaagcc
tggtaaagaagacaacaaaaacctggtaaagaagatggcaacaagcctggt
aaagaagacaacaaaaacctggtaaagaagacggcaacaagcctggcaaag
aagatggcaacaaacctggtaaagaagatggtaacggagtacatgtcgttaa
acctggtgatacagtaaatgacattgcaaaagcaaacggcactactgctgac
aaaattgctgcagataacaaa (SEQ ID NO:22)
```

Fig. 13

NUCLEIC ACIDS ENCODING RECOMBINANT PROTEIN A

CROSS-REFERENCE TO RELATED APPLICATIONS

This application claims priority to U.S. Application Ser. No. 60/873,191, filed on Dec. 6, 2006, the entire contents of which are incorporated herein by reference.

TECHNICAL FIELD

This invention relates to novel nucleic acids that encode truncated recombinant protein A polypeptides, vectors, cells, and methods of use.

BACKGROUND

Staphylococcal Protein A (SPA) is a protein that is found in nature anchored to the outer membrane of the gram-positive *Staphylococcus aureus* bacterium, the organism which is commonly associated with medically significant human "Staph" infections. The role of SPA in the life cycle of *S. aureus* remains uncertain, but some studies have correlated the presence of SPA with pathogenicity of the organism.

Functionally, SPA is well known for its ability to tightly, but reversibly, bind to the constant region of an immunoglobulin molecule (IgG). This property has been widely exploited in the affinity purification of antibodies for commercial uses. For example, SPA can be purified from *S. aureus* and covalently bound to various forms of solid supports to thus immobilize it to make an affinity chromatography resin. Crude preparations of antibodies can then be passed over such an immobilized SPA resin to bind and capture the commercially valuable antibody, while contaminating materials are washed away. The bound antibody may then be eluted in pure form by a simple adjustment of the pH.

SUMMARY

The invention is based, at least in part, on new recombinant nucleic acid sequences encoding truncated versions of protein A polypeptides (e.g., rSPA) that (i) include some portion (but not all) of the X-domain of native protein A, (ii) do not include a signal sequence and (iii) bind specifically to an Fc region of an IgG immunoglobulin. The new nucleic acids have the advantage of being suitable for use in efficiently expressing a truncated form of protein A polypeptides in non-pathogenic bacteria, especially *E. coli*, without being significantly degraded within the bacteria. Thus, the nucleic acids described herein can be used in laboratory and/or manufacturing practices that do not require a pathogenic *S. aureus* host for the production of protein A polypeptides. The truncated rSPA that is encoded by said the new nucleic acid sequences has the useful advantage that it contains some portion of the X domain, which portion significantly improves its ability to be immobilized for use as an affinity chromatography reagent. A means of efficiently producing a form of rSPA that contains some portion of the X domain in *E. coli* or other non-pathogenic bacteria, has not previously been disclosed.

In one aspect, the invention features isolated nucleic acid molecules that include a nucleic acid sequence encoding truncated *Staphylococcus aureus* protein A polypeptides. The protein A polypeptides have one or more of the following features: (i) includes less than a complete native X domain; (ii) does not include a signal sequence (e.g., the nucleotide does not encode a signal sequence) or a heterologous N-terminal sequence; (iii) binds specifically to an Fc region of an IgG immunoglobulin; (iv) is not substantially degraded when expressed in a heterologous host (e.g., a non-Staphylococcal host such as *E. coli*); and (v) includes only Staphylococcal polypeptide sequences. The coding sequence can be codon-optimized for expression in a non-pathogenic organism (e.g., *E. coli*). In some embodiments, the nucleic acid includes a sequence at least 80% identical (e.g., at least 85%, 90%, 95%, 98%, 99%, or 100% identical) to SEQ ID NO:1, SEQ ID NO:2, or SEQ ID NO:22. The nucleic acid sequence can be operably linked to a bacterial ribosome binding site, e.g., ACGCGTGGAGGATGATTAA (SEQ ID NO:3). In some embodiments, the protein A polypeptides bind to the Fc region of human IgG1 with an affinity of 1000 nM or less (e.g., 500 nM or less, 200 nM or less, 50 nM or less, 20 nM or less, 10 nM or less, or 5 nM or less) in 0.02 M sodium phosphate, pH 7.0.

The invention also features isolated nucleic acid molecules that encode a polypeptide, which include one or more nucleic acid sequences encoding an *S. aureus* protein A Ig-binding domain and a portion of an *S. aureus* protein A X-domain, wherein the nucleic acid sequence encoding the portion of the X-domain has a stop codon at position 379, 382, 385, 388, 391, 394, 397, 400, 403, 406, or 409 of the X domain coding sequence. In some embodiments, the one or more sequences encoding an Ig binding domain are wild-type. In other embodiments, the one or more sequence encoding an Ig binding domain are codon-optimized. In some embodiments, the sequence encoding the X domain is "wild-type" except for the stop codon. In other embodiments, the sequence encoding the X domain is codon-optimized. In some embodiments, the polypeptide sequence contains only amino acid sequences found in a native *Staphylococcus* derived protein A.

In another aspect, the invention features vectors that include any of the nucleic acid molecules described herein. The vectors can be expression vectors, wherein the polypeptide-encoding nucleic acid sequences are operably linked to expression control sequences (e.g., a promoter, activator, or repressor). The invention also features bacterial cells, e.g., non-pathogenic bacterial cells (e.g., *E. coli*), that include the above vectors and bacterial cells that include polypeptide-encoding nucleic acid sequences described herein operably linked to an expression control sequence. In other embodiments, the invention also features bacterial cells, e.g., non-pathogenic bacterial cells (e.g., *E. coli*) transformed with the above vectors, and the progeny of such cells, wherein the cells express a truncated protein A or a polypeptide that includes a protein A Ig-binding domain and a portion of a protein A X domain.

The invention also features *E. coli* cells that include an exogenous nucleic acid molecule that encodes a polypeptide that includes SEQ ID NO:5, SEQ ID NO:6, SEQ ID NO:7, or SEQ ID NO:17. In some embodiments, the nucleic acid sequence that encodes the polypeptide is codon-optimized for expression in *E. coli*. In some embodiments, the nucleic acid sequence includes SEQ ID NO:1 or SEQ ID NO:22. In some embodiments, the protein A binds to the Fc region of human IgG1 (e.g., with an affinity of 1000 nM or less (e.g., 500 nM or less, 200 nM or less, 50 nM or less, 20 nM or less, 10 nM or less, or 5 nM or less)) in 0.02 M sodium phosphate, pH 7.0.

In other embodiments, the invention features methods of producing truncated protein A polypeptides that include one or more protein A Ig-binding domains and a portion of a protein A X domain. The methods include culturing any of the cells described herein under conditions permitting expression of the polypeptide. The methods can further include purifying the protein A polypeptide from the cytoplasm of the cell. In some embodiments, the protein A polypeptide is then immobilized on a solid support material, e.g., cellulose, agarose, nylon, or silica. In some embodiments, the solid substrate is a porous bead, a coated particle, or a controlled pore glass. The invention also features solid support materials on which the protein A polypeptide has been immobilized.

The invention also features methods of purifying a protein A polypeptide that includes an Fc region of an IgG immunoglobulin. The methods include contacting the truncated protein A polypeptide-bound substrate made as described herein with a solution that includes a protein that includes an Fc region of an IgG immunoglobulin; washing the substrate; and eluting bound a polypeptide that includes an Fc region of an IgG immunoglobulin. The invention also features protein A polypeptides (e.g., proteins that include an Fc region of an IgG immunoglobulin) purified by the methods described herein or using solid support materials described herein.

As used herein, "truncated protein A polypeptide" refers to a protein A polypeptide that (i) includes some, but not all, of a native X-domain, and (ii) binds specifically to an Fc region of an IgG immunoglobulin.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a schematic map of native protein A domains.

FIG. 2 is an amino acid sequence (SEQ ID NO:4) of native *Staphylococcus aureus* (strain 8325-4) protein A (Lofdahl et al., Proc. Natl. Acad. Sci. USA, 80:697-701, 1983). N-terminal underlined sequence represents *S. aureus* signal peptide. C-terminal underlined sequence represents the X-domain.

FIG. 3 is an example of a protein A amino acid sequence broken into the designated domains: IgG binding E domain (SEQ ID NO:9), IgG binding D domain (SEQ ID NO:10), IgG binding A domain (SEQ ID NO:11), IgG binding B domain (SEQ ID NO:12), IgG binding C domain (SEQ ID NO:13), X domain (X domain 1) (SEQ ID NO:14) and example of portion of X domain used to make recombinant protein shown in FIG. 6 (X domain 2) (SEQ ID NO:15).

FIG. 4 is an amino acid sequence (SEQ ID NO:7) of an exemplary truncated protein A lacking portions of the X domain as seen in FIG. 3 as bolded amino acids. The sequences underlined in SEQ ID NO:7 are repetitive eight amino acid sequences (KPGKEDXX; SEQ ID NO:8).

FIG. 5 is a second example of an amino acid sequence (SEQ ID NO:6) of a recombinant *S. aureus* protein A polypeptide with a portion of the X domain.

FIGS. 6A-6C depict a plasmid map of pREV2.1-rSPA containing genetic elements for expression of the rSPA recombinant gene. Sequence landmarks are noted and include the β-glucuronidase promoter, ribosome binding site (RBS), multiple cloning site (MCS) and Trp terminator. The plasmid backbone is defined as the ~3900 bp DNA sequence between the MluI and BamHI restriction sites.

FIG. 7 is a partial nucleotide sequence (SEQ ID NO:16) of an *E. coli* expression vector. The nucleotide sequence includes a portion of the vector backbone at 5' and 3' terminal sequences (italics), the promoter sequence is underlined, and the start methionine and the termination codon are in bold.

FIG. 8 is a depiction of an immunoblot using antibodies that bind specifically to recombinant protein A polypeptides produced in *E. coli* cells. Lane 1: rPA50; Lane 2: vector control; Lane 3; clone 7a; Lane 4: clone 9a; Lane 5: clone 10a; Lane 6: clone 19a.

FIG. 10 is an exemplary nucleotide sequence (SEQ ID NO:2) that encodes a truncated protein A polypeptide.

FIG. 11 is an amino acid sequence (SEQ ID NO:17) of an exemplary truncated protein A polypeptide lacking a portion of the X domain.

FIG. 12 is an amino acid sequence (SEQ ID NO:5) of an exemplary truncated protein A polypeptide lacking a portion of the X domain.

FIG. 13 is an exemplary nucleic acid sequence (SEQ ID NO:22) encoding a truncated protein A polypeptide.

DETAILED DESCRIPTION

Figure 6A:
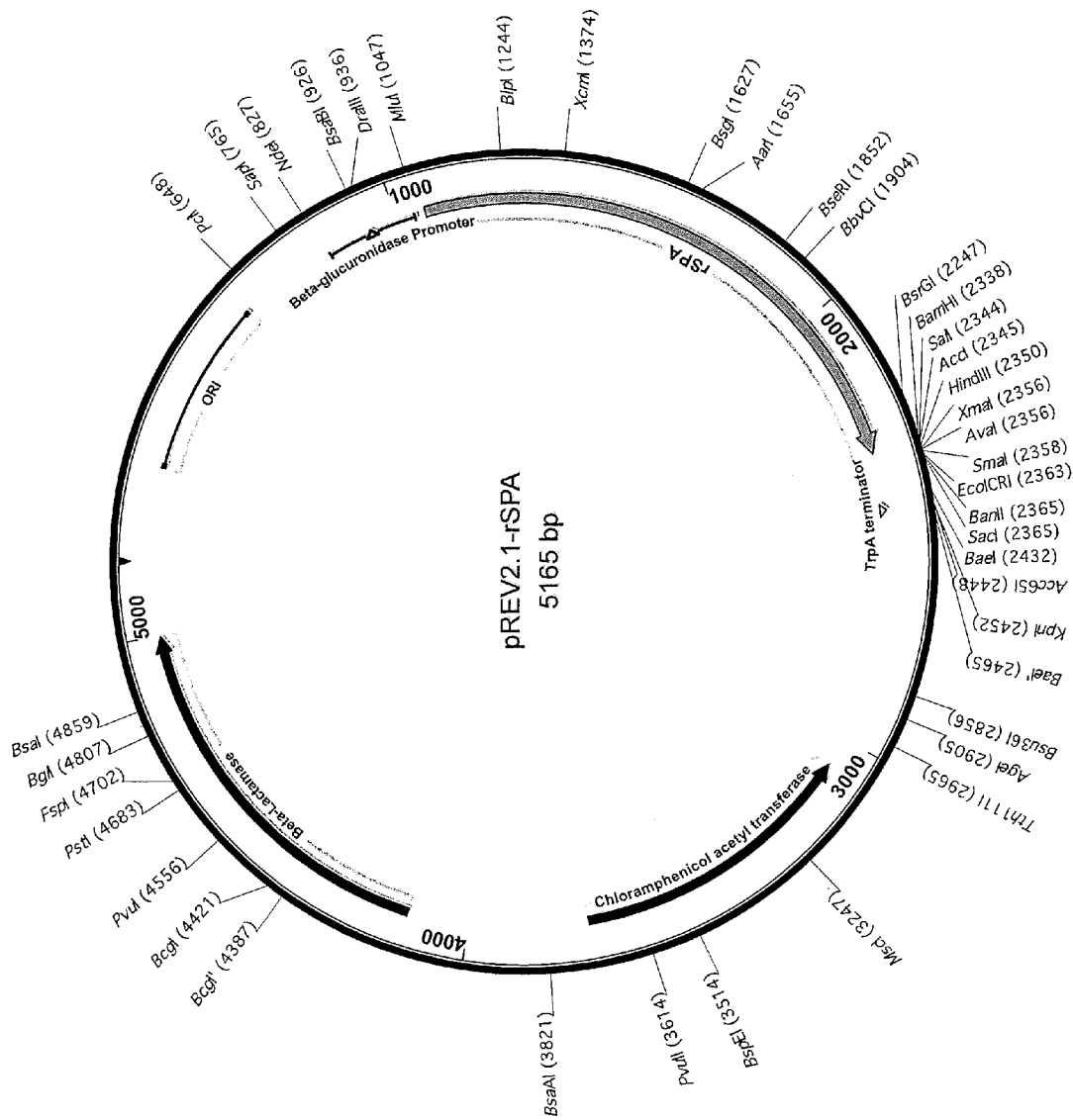
Figure 6C:
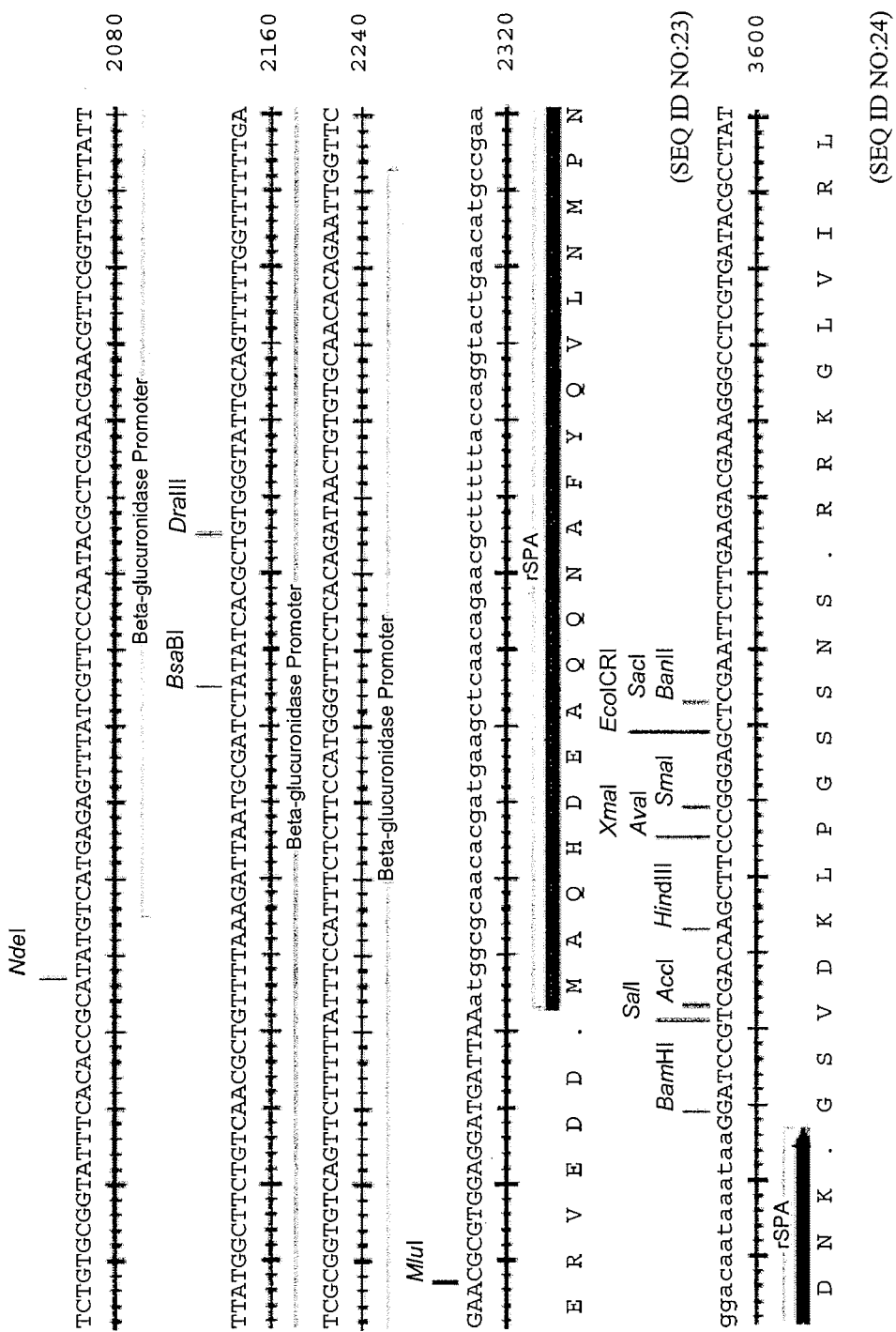

Described herein are novel nucleic acids and methods for the expression of truncated forms of protein A that include some portion, but less than all, of the native X-domain, only polypeptide sequences found in native *S. aureus* protein A, and bind specifically to IgG immunoglobulin Fc region. The truncated forms of protein A can be expressed cytoplasmically (e.g., without a signal peptide) and harvested from a non-pathogenic host, for example, non-pathogenic strains of *E. coli*, which are generally considered safer to handle and use than *S. aureus*. Furthermore, molecular biological and fermentation techniques for *E. coli* have been developed that permit high levels of truncated protein A expression and recovery.

Structure of Full Length Protein A Precursor

SPA is a cell surface protein that can be isolated from particular strains of *Staphylococcus aureus*. The protein is able to bind free IgG and IgG-complexes. Membrane-bound protein A has been identified in the following *S. aureus* strains: NCTC 8325-4 (Iordanescu and Surdeanu, *J. Gen. Microbiol.*, 96:277-281, 1976), NCTC 8530, i.e., CowanI or ATCC 12598; and SA113 or ATCC 35556. A soluble form of protein A is expressed by *S. aureus* strain A676 (Lindmark et al., *Eur. J. Biochem.*, 74:623-628, 1977). The ATCC strains described herein, as well as other *S. aureus* strains, are available from American Tissue Culture Collection (Bethesda, Md.).

The gene encoding the full length SPA precursor is known as spa. Nucleotide and protein sequences for spa are publicly available, e.g., through GENBANK nucleotide database at Accession No. J01786 (complete coding sequence) and/or BX571856.1 (genomic sequence of clinical *S. aureus* strain that includes coding sequence for GENPEPT Accession No. CAG39140). See also, U.S. Pat. No. 5,151,350. In spite of the various sequences available to the public, the inventors believe that the new nucleic acid sequences described herein have not been previously isolated, sequenced, or publicly described.

Structurally, the SPA protein consists of an amino-terminal signal peptide followed by five highly homologous immunoglobulin binding domains and a so-called X domain (see FIG. 1). The signal peptide directs the SPA protein for secretion through the membrane and is thereafter removed by proteolysis. The five immunoglobulin binding domains, named A through E, are arranged as E-D-A-B-C in most naturally occurring forms of the molecule. The X domain, which lies at the carboxy terminus and is believed to be involved in anchoring the SPA to and extending it from the outer membrane of the bacterium, consists of two structurally distinct regions, the first of which comprises a series of highly repetitive blocks of octapeptide sequence (termed Xr) and the second of which is a hydrophobic region at the extreme C-terminus (termed Xc), which is thought to anchor the SPA molecule into the cell membrane. The entire SPA molecule thus consists of seven distinct domains that are structurally arranged as [S]-E-D-A-B-C-X.

A number of strains of S. aureus are known and the protein sequence of the SPA from several of these has been reported in the prior art. A comparison of these SPA sequences reveals a significant amount of genetic variability from one strain to another, which can include point mutations, domain deletions, repetitive sequence insertions, and genetic rearrangements. The effect of such differences on SPA function has not been well studied, although it appears that deletion of at least a portion of the Xc domain results in a form of SPA that is secreted into the culture medium (Lindmark et al., Eur. J. Biochem., 74:623-628, 1977).

The IgG Fc region-binding domains of S. aureus include highly repetitive sequences at the protein level and, to a lesser extent, at the nucleic acid sequence level. Strain 8325-4 produces protein A that includes five IgG-binding domains that are schematically represented in FIG. 1 as regions E, D, A, B, and C. These domains bind specifically to the Fc and/or Fab portion of IgG immunoglobulins to at least partly inactivate an S. aureus-infected host's antibodies. By binding to the Fc region of immunoglobulins, protein A inhibits binding of IgGs to complement and Fc receptors on phagocytic cells, thus blocking complement activation and opsonization.

The X domain is a C-terminal region that contains (i) Xr, a repetitive region with approximately twelve repetitive eight amino acid sequences and (ii) Xc, an approximately 80 to 95 amino acid constant region at the C-terminus of the protein. Each repetitive amino acid sequence generally includes a KPGKEDXX (SEQ ID NO:8) motif, wherein in some embodiments the XX dipeptide can be NN, GN, or NK. See e.g., Uhlen et al., J. Biol. Chem. 259:1695-1702, 1984, and underlined residues in FIG. 5. The X domain is involved in the targeting and anchoring protein A to the cell surface of S. aureus.

Although the X domain is not involved in IgG binding, it may be useful to retain a portion of the X domain (e.g., when expression protein A polypeptide by recombinant means) for the purpose of improving the properties of the rSPA in the preparation of an affinity chromatography resin. For example, a portion of the X domain can serve as a "molecular stalk" to tether the IgG-binding regions of the polypeptide to a solid substrate. Moreover, a portion of the X domain can act to present the IgG-binding regions of the polypeptide at a distance out and away from a solid substrate to which it is tethered in order to better allow interactions of the IgG-binding regions to Fc-containing polypeptides. Further, the inclusion of a portion of the X domain can potentially improve folding and/or stability of the protein A molecule over the folding and/or stability of the protein A molecule without the X domain. Finally, certain of the amino acid side chains, e.g., lysine, present in the X domain can provide convenient reaction sites to enable efficient covalent coupling to a solid support without compromising the functional properties of the IgG binding domains.

The signal peptide (SP) is an N-terminal extension present in proteins destined for export by the general (Sec-dependent) bacterial secretion system. SP mediates recognition of the nascent unfolded polypeptide chain by the Sec-dependent secretion apparatus, translocation through the cell membrane, and cleavage by the signal peptidase (reviewed by van Wely et al., FEMS Microbiol. Rev., 25:437-54, 2001). Secretion is sometimes necessary to achieve stable polypeptide expression. Cytoplasmic expression of recombinant proteins may fail because of toxicity of the protein, a requirement of the secretion process for proper folding of the protein, or instability of the protein in the cytoplasmic environment. Stable recombinant protein expression can sometimes achieved by enclosing the polypeptide sequence of interest with flanking regions of heterologous amino acids.

While it may be desirable to express an rSPA that contains at least a portion of the X domain, no demonstration of such a protein being produced free of heterologous sequences has been reported. Attempts to produce a recombinant protein A containing a portion of the X domain by secretion in E. coli produced a protein product that was extensively degraded by endogenous proteases (Uhlen et al., J. Bacteriol., 159:713-719, 1984). Another challenge that has been noted in attempting to express a full-length rSPA gene product in E. coli is that the Xc region can be toxic to the cells (Wames et al., Curr. Microbiol., 26:337-344, 1993). These findings have led at least some investigators to eliminate the X domain when expressing the rSPA gene in E. coli (see, e.g., Hellebust et al., J. Bacteriol. 172:5030-34, 1990). The new sequences and systems described herein provide for high levels of expression in E. coli of proteolytically stable forms of rSPA that contain a portion of the X domain. These X domain containing forms of rSPA have particular utility in the creation of rSPA containing affinity chromatography resins.

Virulence of S. aureus

The Center for Disease Control and World Health Organization classify S. aureus a Biosafety Level II or Group II infectious agent, respectively. These classifications are reserved for agents associated with human disease and hazards of percutaneous injury, ingestion, and/or mucous membrane exposure.

S. aureus is a major cause of hospital-acquired (nosocomial) infections associated with surgical wounds and implanted medical devices. This bacterium can release enterotoxins responsible for food poisoning, and superantigens released by S. aureus can induce toxic shock syndrome. S. aureus also causes a variety of suppurative (pus-forming) infections and toxinoses in humans, as well as skin lesions including boils, styes, and furunculosis. S. aureus has also been found to co-infect subjects with pneumonia, mastitis, phlebitis, meningitis, urinary tract infections, and deep-seated infections, such as osteomyelitis and endocarditis.

S. aureus expresses a number of potential virulence factors: (1) surface proteins that promote colonization of host tissues; (2) invasins (e.g., leukocidin, kinases, hyaluronidase) that promote bacterial spread in tissues; (3) surface factors (e.g., capsule, protein A) that inhibit phagocytic engulfment; (4) biochemical properties that enhance their survival in phagocytes (carotenoids, catalase production); (5) immunological disguises (protein A, coagulase, clotting factor); (6) membrane-damaging toxins that lyse eukaryotic cell membranes (hemolysins, leukotoxin, and leukocidin); (7) exotoxins that damage host tissues or otherwise provoke symptoms of disease (staphylococcal enterotoxins (SE) A-G, toxic shock syndrome toxin (TSST), exfoliative toxin (ET)); and (8) inherent and acquired resistance to antimicrobial agents.

Thus, the virulence level of *S. aureus* is more severe than that for Biosafety Level 1 or Group 1 organisms, such as laboratory and commercial strains of *E. coli*. Biosafety Level 1 is reserved for well-characterized organisms not known to cause disease in healthy adult humans, and of minimal potential hazard to laboratory personnel and the environment.

Nucleic Acids Encoding Truncated Protein A Polypeptides

In one aspect, described herein are certain nucleic acids encoding a truncated protein A polypeptide that has one or more of the following characteristics: (i) contains only sequences coding for SPA, i.e., does not contain heterologous sequences, (ii) includes some portion of, but less than all of, the complete native X domain, (iii) binds specifically to an IgG immunoglobulin Fc region, and (iv) lacks a signal sequence. Exemplary nucleic acids include, but are not limited to, nucleic acids encoding SEQ ID NO:1 and variants thereof that have been codon optimized for expression in a specific host such as *E. coli*.

An exemplary nucleic acid encoding a truncated *S. aureus* protein A polypeptide is as follows.

```
                                                    (SEQ ID NO:1)
ATGGCGCAACACGATGAAGCTCAACAGAACGCTTTTTACCAGGTACT

GAACATGCCGAACCTGAACGCGGATCAGCGCAACGGTTTCATCCAGA

GCCTGAAAGACGACCCTTCTCAGTCCGCAAACGTTCTGGGCGAGGCT

CAGAAACTGAACGACAGCCAGGCCCCAAAAGCAGATGCTCAGCAAAA

TAACTTCAACAAGGACCAGCAGAGCGCATTCTACGAAATCCTGAACA

TGCCAAATCTGAACGAAGCTCAACGCAACGGCTTCATTCAGTCTCTG

AAAGACGATCCGTCCCAGTCCACTAACGTTCTGGGTGAAGCTAAGAA

GCTGAACGAATCCCAGGCACCAAAAGCAGACAACAACTTCAACAAAG

AGCAGCAGAACGCTTTCTATGAAATCTTGAACATGCCTAACCTGAAT

GAAGAACAGCGTAACGGCTTCATCCAGTCTCTGAAGGACGACCCTAG

CCAGTCTGCTAACCTGCTGTCCGAAGCAAAAAAACTGAACGAGTCCC

AGGCTCCAAAAGCGGATAACAAATTCAACAAGGAGCAGCAGAACGCA

TTCTACGAAATCCTGCACCTGCCGAACCTGAACGAAGAACAGCGTAA

CGGTTTCATCCAATCCCTGAAAGACGATCCTTCCCAGTCCGCAAATC

TGCTGGCAGAAGCAAAGAAACTGAACGACGCACAGGCACCGAAGGCT

GACAACAAGTTCAACAAAGAGCAGCAGAATGCCTTCTACGAGATTCT

GCATCTGCCAAACCTGACTGAGGAGCAGCGCAACGGTTTCATTCAGT

CCCTGAAGGACGACCCAAGCGTCAGCAAGGAAATCCTGGCTGAGGCG

AAAAAACTGAACGATGCACAGGCTCCGAAGGAAGAAGACAACAATAA

ACCTGGTAAAGAAGATAATAATAAGCCTGGCAAGGAAGATAACAACA

AGCCGGGCAAGGAGGACAACAATAAACCGGGCAAGAGGATAATAAC

AAGCCTGGTAAGGAAGACAACAACAAACCAGGCAAAGAAGATGGCAA

CAAGCCGGGTAAGGAGGATAATAAAAAACCAGGCAAGGAAGACGGCA
```

```
                                                    -continued
ACAAACCTGGCAAGGAGGATAACAAAAAGCCAGGCAAGGAGGATGGT

AATAAACCGGGCAAAGAAGACGGCAACAAGCCTGGTAAAGAAGACGG

TAACGGTGTACACGTCGTTAAACCTGGTGACACCGTGAACGACATCG

CTAAGGCTAATGGCACCACGGCAGACAAGATTGCAGCGGACAATAAA

TAA
```

For both SEQ ID NO:1 and SEQ ID NO:22, the E domain is encoded by nucleotides 2-171; the D domain is encoded by nucleotides 172-354; the A domain is encoded by nucleotides 355-528; the B domain is encoded by nucleotides 529-702; the C domain is encoded by nucleotides 703-876; and the X domain is encoded by nucleotides 877-1272.

Certain genes can provide challenges for efficient expression by recombinant means in heterologous hosts. Alteration of the codons native to the sequence can facilitate more robust expression of these proteins. Codon preferences for abundantly expressed proteins have been determined in a number of species, and can provide guidelines for codon substitution. Synthesis of codon-optimized sequences can be achieved by substitution of codons in cloned sequences, e.g., by site-directed mutagenesis, or by construction of oligonucleotides corresponding to the optimized sequence by chemical synthesis. See, e.g., Mirzabekov et al., J. Biol. Chem., 274:28745-50, 1999.

The optimization should also include consideration of other factors such as the efficiency with which the sequence can be synthesized in vitro (e.g., as oligonucleotide segments) and the presence of other features that affect expression of the nucleic acid in a cell. For example, sequences that result in RNAs predicted to have a high degree of secondary structure should be avoided. AT- and GC-rich sequences that interfere with DNA synthesis should also be avoided. Other motifs that can be detrimental to expression include internal TATA boxes, chi-sites, ribosomal entry sites, prokaryotic inhibitory motifs, cryptic splice donor and acceptor sites, and branch points. These features can be identified manually or by computer software and they can be excluded from the optimized sequences.

Nucleic acids described herein include recombinant DNA and synthetic (e.g., chemically synthesized) DNA. Nucleic acids also include recombinant RNAs, e.g., RNAs transcribed (in vitro or in vivo) from the recombinant DNA described herein, or synthetic (e.g., chemically synthesized) RNA.

Nucleic acids can be double-stranded or single-stranded. Where single-stranded, the nucleic acid can be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have increased resistance to nucleases.

The term "purified," referring, e.g., to a polypeptide, denotes a molecule that is substantially free of cellular or viral material with which it is naturally associated or recombinantly expressed, or chemical precursors or other chemicals used for chemical synthesis.

Also described herein are variants of nucleic acids encoding truncated rSPA molecules. Such variants code for IgG-binding, truncated versions of protein A polypeptides that (i) include a portion of but less than the complete X domain of SPA, (ii) are suitable for expression in *E. coli*, and (iii) are substantially identical to SEQ ID NO:6 or SEQ ID NO:7. In some embodiments, the nucleic acids do not encode a signal sequence. A variant nucleic acid (e.g., a codon-optimized nucleic acid) encoding a truncated protein A molecule can be substantially identical, i.e., at least 75% identical, e.g., 80%, 85%, 90%, 91%, 92%, 93%, 94%, 95%, 96%, 97%, 98%, 99%, or 99.5% identical, to SEQ ID NO:1 or SEQ ID NO:22. In certain embodiments, a truncated rSPA variant that is "substantially identical" to SEQ ID NO:6 or SEQ ID NO:7 is a polypeptide that is at least 75% identical (e.g., at least about 80%, 85%, 90%, 91%, 92%, 93%, 94%, 95%, 96%, 97%, 98%, 99%, or 99.5% identical) to a SEQ ID NO:6 or SEQ ID NO:7.

The determination of percent identity between two nucleotide or polypeptide sequences can be accomplished using the BLAST 2.0 program, which is available to the public at ncbi.nlm.nih.gov/BLAST. Sequence comparison is performed using an ungapped alignment and using the default parameters (gap existence cost of 11, per residue gap cost of 1, and a lambda ratio of 0.85). When polypeptide sequences are compared, a BLOSUM 62 matrix is used. The mathematical algorithm used in BLAST programs is described in Altschul et al., 1997, Nucleic Acids Research, 25:3389-3402.

Nucleic acid variants of a sequence that contains SEQ ID NO:1, SEQ ID NO:2, or SEQ ID NO:22 include nucleic acids with a substitution, variation, modification, replacement, deletion, and/or addition of one or more nucleotides (e.g., 2, 3, 4, 5, 6, 8, 10, 12, 15, 20, 25, 30, 35, 40, 50, 60, 70, 80, 90, or 100 nucleotides) from a sequence that contains SEQ ID NO:1, SEQ ID NO:2, or SEQ ID NO:22. All of the aforementioned nucleic acid variants encode a recombinant truncated polypeptide that (i) is suitable for expression in a non-pathogenic, heterologous host cell, (ii) contains a portion of, but less than all of, the complete X-domain of SPA, and (iii) specifically binds to IgG. In particular, the term "variant" covers nucleotide sequences encoding polypeptides that are capable of binding to IgG through introduction of additional S. aureus protein A derived polypeptide sequences, for example, from additional strains of S. aureus.

Vectors, Plasmids, and Host Cells

Nucleic acids encoding a truncated rSPA polypeptide as described herein can be operably linked to genetic constructs, e.g., vectors and plasmids. In some cases a nucleic acid described herein is operably linked to a transcription and/or translation sequence in an expression vector to enable expression of a truncated rSPA polypeptide. By "operably linked," it is meant that a selected nucleic acid, e.g., a coding sequence, is positioned such that it has an effect on, e.g., is located adjacent to, one or more sequence elements, e.g., a promoter and/or ribosome binding site, which directs transcription and/or translation of the sequence.

Some sequence elements can be controlled such that transcription and/or translation of the selected nucleic acid can be selectively induced. Exemplary sequence elements include inducible promoters such as tac, T7, $P_{BAD}$ (araBAD), and β-D-glucuronidase (uidA) promoter-based vectors. Control of inducible promoters in E. coli can be enhanced by operably linking the promoter to a repressor element such as the lac operon repressor ($lac^R$). In the specific case of a repressor element, "operably linked" means that a selected promoter sequence is positioned near enough to the repressor element that the repressor inhibits transcription from the promoter (under repressive conditions).

Typically, expression plasmids and vectors include a selectable marker (e.g., antibiotic resistance gene such as $Tet^R$ or $Amp^R$). Selectable markers are useful for selecting host cell transformants that contain a vector or plasmid. Selectable markers can also be used to maintain (e.g., at a high copy number) a vector or plasmid in a host cell. Commonly used bacterial host plasmids include pUC series of plasmids and commercially available vectors, e.g., pAT153, pBR, PBLUESCRIPT, pBS, pGEM, pCAT, pEX, pT7, pMSG, pXT, pEMBL. Another exemplary plasmid is pREV2.1.

Plasmids that include a nucleic acid described herein can be transfected or transformed into host cells for expression of truncated rSPA polypeptides. Techniques for transfection and transformation are known in the art, including calcium phosphatase transformation and electroporation. In certain embodiments, transformed host cells include non-pathogenic prokaryotes capable of highly expressing recombinant proteins. Exemplary prokaryotic host cells include laboratory and/or industrial strains of E. coli cells, such as BL21 or K12-derived strains (e.g., C600, DH1α, DH5α, HB101, INV1, JM109, TB1, TG1, and X-1Blue). Such strains are available from the ATCC or from commercial vendors such as BD Biosciences Clontech (Palo Alto, Calif.) and Stratagene (La Jolla, Calif.). For detailed descriptions of nucleic acid manipulation techniques, see Ausubel et al., eds., Current Protocols in Molecular Biology, Wiley Interscience, 2006, and Sambrook and Russell, Molecular Cloning: A Laboratory Manual, Cold Spring Harbor Press, NY, 2001.

Expression and Purification of Truncated Protein A Polypeptides

Host cells containing a nucleic acid encoding a truncated rSPA can be grown under conditions suitable for expression of said encoded truncated rSPA. Host cells can be grown that constitutively express truncated rSPA. In other systems, host cells are first grown under conditions that inhibit expression of truncated rSPA and are later switched to media that induces expression of truncated rSPA, for example, by activating or derepressing promoter operably linked to the rSPA coding sequence.

In another exemplary system, a bacterial host cell includes the coding sequence for a truncated rSPA (operably linked to T7 promoter), a T7 RNA polymerase (operably linked to lac operon/lac promoter control region), and a lac repressor (lacI gene). The lac repressor can bind to the lac operon and prevent bacterial RNA polymerase binding to the lac promoter region, thereby inhibiting T7 polymerase expression. Bacterial host cells can be cultured, e.g., in fermentation tanks. When the host culture reaches a desired population density (e.g., population reaches exponential or "log" growth), isopropyl-beta-D-thiogalactopyranoside (IPTG) is added to the bacterial growth media. IPTG binds to and inactivates the lac repressor, thereby derepressing the lac operon/lac promoter and allowing expression of T7 polymerase. T7 polymerase expression, in turn, can drive high level expression of truncated rSPA.

After host cells have been grown under conditions suitable for expression of truncated rSPA, host cells are harvested and rSPA protein is purified from other host cell material. Typically, host cells are lysed in the presence of protease inhibitors and truncated rSPA is separated from cell debris, e.g., by low speed centrifugation. Further enrichment of rSPA material is optionally accomplished by serial centrifugations and isolation of fractions containing rSPA.

In certain embodiments, purification of truncated rSPA includes binding to purification media such as a resin or magnetic beads. In these embodiments, purification media includes IgG, or fragments thereof, that bind to protein A. IgG fragments that bind to protein A include Fc or Fab fragments. In other embodiments, purification media includes nickel-nitrilotriacetic acid (Ni-NTA), maltose, glutathione, or any other material that binds to a truncated rSPA fusion protein.

After binding of truncated rSPA to purification media, the purification media is washed, e.g., with a salt buffer or water, and truncated rSPA is eluted from the purification media with an elution buffer. Elution buffer includes a composition that disrupts truncated rSPA binding to the purification media. For example, elution buffers can include glycine to disrupt IgG-truncated protein A interactions, imidazole or urea to disrupt His-tag-Ni-NTA interactions, and/or glutathione to disrupt GST-glutathione interactions. Truncated rSPA is recovered by batch or column elution.

Eluted rSPA can be further purified using chromatography techniques, e.g., ion exchange chromatography, affinity chromatography, gel filtration (or size exclusion) chromatography. In addition, purified truncated rSPA can be concentrated by binding a solution of purified rSPA to purification media and subsequently eluting bound truncated rSPA in a smaller volume of elution buffer.

For detailed protein purification techniques, see Scopes, Protein Purification: Principles and Practice, Springer Science, NY, 1994.

Substrates

Described herein are new methods of making useful resins and other substrates to which truncated rSPA can be attached. Generally, a nucleic acid described herein is used to express truncated rSPA, which is purified, and subsequently attached to a substrate. Substrates can include organic and inorganic materials. Substrates can be manufactured in useful forms such as microplates, fibers, beads, films, plates, particles, strands, gels, tubing, spheres, capillaries, pads, slices, or slides. Substrate material can include, for example, magnetic beads, porous beads (e.g., controlled pore glass beads), cellulose, agarose (e.g., SEPHAROSE™), coated particles, glass, nylon, nitrocellulose, and silica.

In some embodiments, truncated rSPA is expressed in a non-pathogenic host from a nucleic acid described herein, the rSPA is purified from host material, and the rSPA is attached (e.g., covalently attached) to a porous substrate that is hydrophobic and/or protein absorptive. Such substrates or supports include ion exchange packings and bioaffinity packings.

In certain embodiments, truncated rSPA is harvested and purified as described herein from a non-pathogenic organism, and the rSPA is attached to a porous protein-adsorptive support having hydroxyl groups on its surface. Exemplary supports include porous metalloid oxides, porous metallic oxides, and porous mixed metallic oxides. Such materials include silica, e.g., silica particles or silica gel, alumina, stannia, titania, zirconia, and the like. In some embodiments, the porous support has a particle size of about 0.5 to about 800 micrometers, e.g., about 5 to about 60 micrometers, and a pore diameter of about 30 to about 300 angstroms, e.g., about 60 angstroms.

1. Exemplary Substrates

Porous Silica (Including Controlled Pore Glass)

Porous silica, including controlled pore glass, has been described in U.S. Pat. Nos. 3,549,524 and 3,758,284 and is commercially available from vendors such as Prime Synthesis, Inc. (Aston, Pa.) and Millipore (Billerica, Mass.). Porous silica supports may undergo various treatments prior to being attached to truncated protein A polypeptides. Generally, a silica support is derivatized to introduce reactive functional groups. The derivatized support is activated and then coupled to truncated rSPA produced by the methods described herein.

For example, silica supports can be derivatized using an arginine-containing linker as described in U.S. Pat. No. 5,260,373. Silica supports can be amino-derivatized by a silanization process, e.g., using aminosilanes such as γ-aminopropyltrimethoxysilane 6-(aminohexylaminopropyl)trimethoxy silane, aminoundecyltrimethoxysilane, p-aminophenyltrimethoxysilane, 4-aminobutyltrimethoxysilane, and (aminotheylaminoethyl)-phenyltrimethoxysilane. Dual zone silanization can be employed, e.g., as described in U.S. Pat. Nos. 4,773,994, 4,778,600, 4,782,040, 4,950,634, and 4,950,635. Silica supports can also be amino-derivatized using o-dianisidine, e.g., as described in U.S. Pat. No. 3,983,000. Amino-derivatized supports can be carboxy-derivatized by a second reaction with, e.g., succinic anhydride, e.g., as described in U.S. Pat. No. 4,681,870. Amino-derivatized supports can also be treated with an aldehydes, e.g., gluteraldehyde, to introduce reactive aldehyde groups, as described in U.S. Pat. Nos. 3,983,000 and 4,681,870. Derivatized porous silica can also be obtained commercially from Prime Synthesis, Inc.

Derivatized porous silica can be activated and reacted and bound to truncated rSPA in aqueous solution. For example, aqueous peptide solutions react directly with o-dianisidine and/or gluteraldehyde coated substrates. In other examples, carbodiimide and rSPA are mixed with derivatized substrate, such that carbodiimide reacts with and attaches rSPA to the derivatized substrate, e.g., as described in U.S. Pat. No. 4,681,870.

Other methods for attaching a peptide to porous silica can also be used in the methods described.

2. Exemplary Substrates

Agarose

A variety of agarose substrates known in the art can also be used in the methods described herein. For example, agarose substrates (e.g., cross-linked, beaded agarose) suitable for use in chromatography packing resin can be derivatized, activated, and linked to a truncated rSPA produced according to the methods described herein.

Derivatized agarose can be manufactured using methods known in the art. For example, agarose can be derivatized and activated using an arginine-containing linker as described in U.S. Pat. No. 5,260,373. Activated and derivatized agarose products suitable for peptide linking are also commercially available from manufacturers such as Amersham Biosciences (Piscataway, N.J.). These include N-hydroxysuccinimide (NHS)-activated SEPHAROSE™ 4 FAST FLOW designed for the covalent coupling through the primary amine of a ligand, CNBr-activated SEPHAROSE™ designed for the attachment of larger primary amine containing ligands under mild conditions, EAH Sepharose 4B designed for coupling of small ligands containing free carboxyl groups via a 10-atom spacer arm using carbodiimide as the coupling, and ECH Sepharose 4B for coupling small ligands containing free amino groups via a 9-atom spacer arm also using carbodiimide as the coupling reagent. Instructions for coupling derivatized SEPHAROSE™ to peptides can be obtained from the manufacturer.

Generally, truncated rSPA can be coupled to derivatized agarose substrates by incubating rSPA and the activated substrate in an aqueous solution. Coupling conditions can include salt buffers such as 4-(2-hydroxyethyl)-1-piperazine ethanesulfonic acid (HEPES), sodium carbonate, sodium chloride, potassium phosphate and other salts. Carbodiimide can also be used as needed or desired.

Applications For Truncated rSPA Nucleic acids described herein are useful for the cost effective, efficient, and less hazardous production of truncated rSPA in non-pathogenic hosts such as *E. coli* as compared to harvesting of similar peptides from *S. aureus*. The rSPA produced by the nucleic acids described herein can be covalently linked to substrates with greater efficiency than forms of rSPA that are lacking the X domain.

Truncated rSPA can be also used in a wide array of industries including research, medical diagnostics, and the discovery and manufacture of therapeutic biologics. Research applications include use as a reagent in immunoprecipitation and antibody purification protocols. Truncated rSPA can be used as a component in diagnostic tools that isolate or evaluate antibodies in an organism.

Truncated rSPA is particularly useful for the manufacture of affinity chromatography resins that are widely used for large-scale purification of antibodies for human therapeutic use. In these applications, a truncated rSPA containing affinity chromatography resin is contacted with a solution containing a therapeutic antibody as well as undesired contaminating materials to selectively bind the desired antibody to the immobilized rSPA. The rSPA containing affinity chromatography resin with the desired antibody tightly bound to it is first washed to remove the contaminating materials, and then the antibody is eluted from the affinity chromatography resin in purified form by, for example, the use of acidic or high salt elution buffers.

The commercial significance of the therapeutic antibody market is expected to grow quickly in the near future. For example, the global market for therapeutic monoclonal antibodies in 2002 was reportedly above $5 billion and has been projected to approximately triple in size by 2008 to nearly $17 billion. Reichert and Pavlou, *Nature Reviews Drug Discovery,* 3:383-4, 2004. Servicing this market will be benefited by cost-effective tools for large scale, reliable purification of monoclonal antibodies.

The invention is further described in the following examples, which do not limit the scope of the invention described in the claims.

EXAMPLES

Materials and Methods

All enzymes used in the procedures described herein were purchased from New England BioLabs (Ipswich, Mass.). All DNA purification kits were purchased from Qiagen, Inc (Valencia, Calif.). All agarose plates were purchased from Teknova, Inc (Hollister, Calif.). The engineered rSPA-s was synthesized and supplied in the plasmid pJ5:G03257. All *E. coli* hosts were lab strains with the exception of Subcloning Efficiency™ DH5α cells, which were purchased from Invitrogen, Inc (Carlsbad, Calif.).

Preparation of Plasmid DNA Stocks

All liquid cultures were grown overnight for 12-16 hours at 37° C., shaking at 250 RPM in disposable plastic baffled-bottom flasks. All plasmid DNA was isolated using the QIAGEN Plasmid Maxi kit according to manufacturers directions.

The pREV2.1 vector described in WO 90/03984 was digested with HpaI and NruI endonucleases to release the β-glucuronidase signal sequence and a small 3' portion of the β-glucuronidase promoter. The vector was then re-ligated and subsequently digested with MluI and BamHI. As described below, the PCR amplified optimized protein A coding sequence was digested MluI and BamHI and cloned by ligation with T4 ligase into digested pREV2.1 vector to yield the construct pREV2.1-rSPA. FIG. 8 shows a (partial) DNA sequence of the construct, in which the vector sequence is indicated by italics, the promoter sequence is underlined, and the start methionine and the termination codons are in bold.

The pREV2.1-rSPA plasmid served as a source of the pREV2.1 plasmid backbone. A vial of PR13/pREV2.1-rSPA was thawed and used to inoculate 100 mL of Miller LB media (BD Biosciences, San Jose, Calif.) with 34 μg/mL chloramphenicol and 100 μg/mL ampicillin. A HMS174/pET12a glycerol stock was scratched and used to inoculate 100 mL of LB media containing 100 μg/mL of ampicillin.

Preparation of Transformation Competent *E. coli* Host Cells

Both PR13 and BL21(DE3) host *E. coli* (Table 1) were prepared according to an adapted $CaCl_2$ protocol (Elec. J. Biotech., 8:114-120). Briefly, cells were grown under selection to an $OD_{600}$~0.25-0.4, then harvested in 50 mL Oak Ridge tubes (Nalgene, Rochester, N.Y.). Pellets were resuspended in one-half volume ice-cold TB solution (10 mM PIPES, 75 mM $CaCl_2.2H_2O$, 250 mM KCl, 55 mM $MnCl_2$.4H2O, pH 6.7 with KOH) and incubated on ice for 25 minutes. Cells were centrifuged at 8,000 RPM for 1 minute at 4° C., TB was decanted and pellet was resuspended in one-tenth original volume ice-cold TB. Aliquots of 100 μL were snap frozen in liquid nitrogen and stored at −80° C.

TABLE 1

*E. coli* strains described herein

| Strain | Description |
| --- | --- |
| PR13 | Strain of *E. coli* used for protein expression with pREV2.1 expression system (F− thr-1 leuB6(Am) lacY1 rna-19 LAMpnp-13 rpsL132($Str^R$) malT1 ($Lam_R$) xyl-7 mtlA2 thi-1) |
| BLR (DE3) | Strain of *E. coli* used with pET expression system (*E. coli* B F− ompT hsdSB(rB− mB−)gal dcm (DE3) Δ(srlrecA)306::Tn10 ($Tet^R$) |
| DH5α | Strain of *E. coli* used primarily for plasmid maintenance (F− φ80lacZΔM15 Δ(lacZYA-argF)U169 recA1 endA1 hsdR17(rk−, mk+) phoA supE44 thi-1 gyrA96 relA1 λ−) |

Example 1

Recombinant DNA Construct for Expression in *E. coli*

To manufacture truncated rSPA in a host that is less pathogenic than *S. aureus*, a DNA construct was engineered to express a truncated version of strain 8325-4 protein A in *E. coli*. The construct contained a truncated 8325-4 protein A coding sequence including the E, D, A, B, C, and part of the X domains, but missing both the native N-terminal *S. aureus* signal sequence and a portion of the native C-terminal X domain. The DNA construct did not introduce coding sequences for heterologous polypeptides not found in native SPA. The coding sequence was functionally linked to an *E. coli* promoter and *E. coli* ribosome binding site. Restriction digestions and ligations were performed according to manufacturer instructions. PCR amplifications were performed as described below. Ligations were transformed into *E. coli* strain DH5α. DNA sequencing of one of a DH5α clone (18A) was performed under contract with the Iowa State University Sequencing Facility (Ames, Iowa) using the following primers: IPA-1: 5' AAA GCA GAT GCT CAG CAA (SEQ ID NO:18); IPA-2: 5' GAT TTC CTT GCT GAC GCT T (SEQ ID NO:19); Anti-IPA-2: 5' AAG CGT CAG CAA GGA AAT C (SEQ ID NO:20); and BG promoter-2: 5' GAT CTA TAT CAC GCT GTG G (SEQ ID NO:21).

Example 2
Expression of Truncated rSPA in *E. coli*

The ability of four independent DH5α clones (labeled PA/pREV 7a, 9a, 10a, and 18a) harboring the construct described in Example 1 to express recombinant truncated rSPA was evaluated by SDS-PAGE and Western Blotting. Total cell lysates from *E. coli* were electrophoresed on SDS-PAGE gels. Samples were analyzed by SDS-PAGE as described above.

Figure 8:
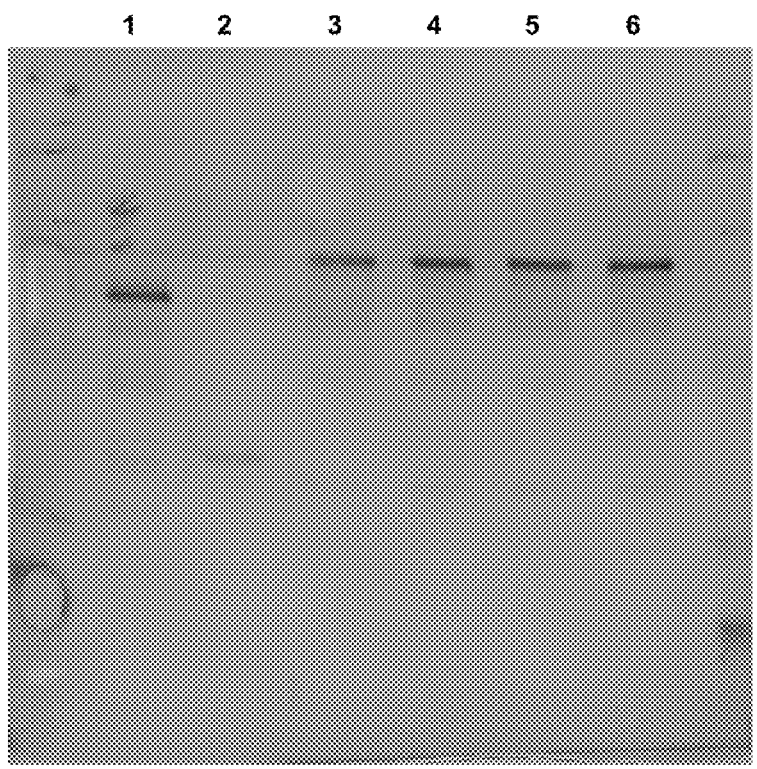
Figure 9A:
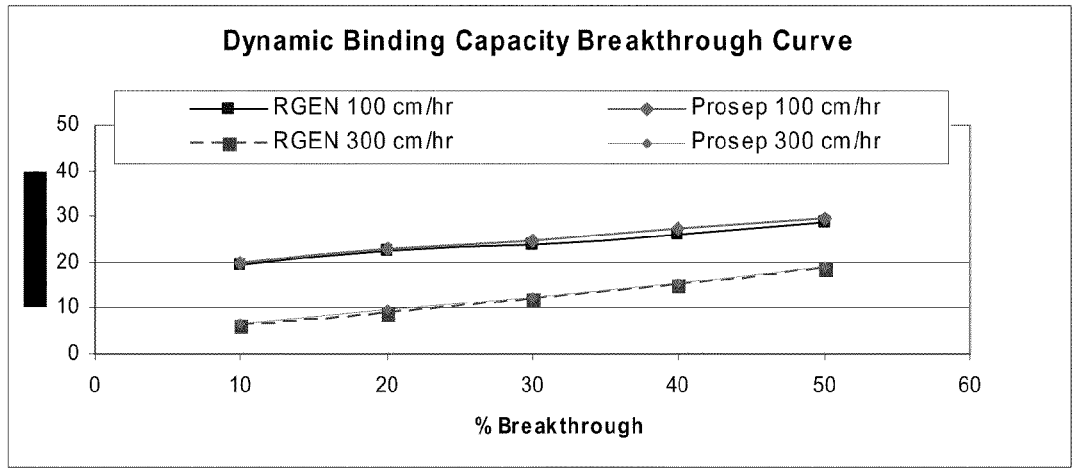
FIGS. 9A-B are graphs comparing the results of dynamic binding capacity experiments using (i) truncated protein A polypeptide produced using a nucleic acid described herein and (ii) PROSEP™ A chromatography media (Millipore) as a commercially available comparison.
Figure 9B:
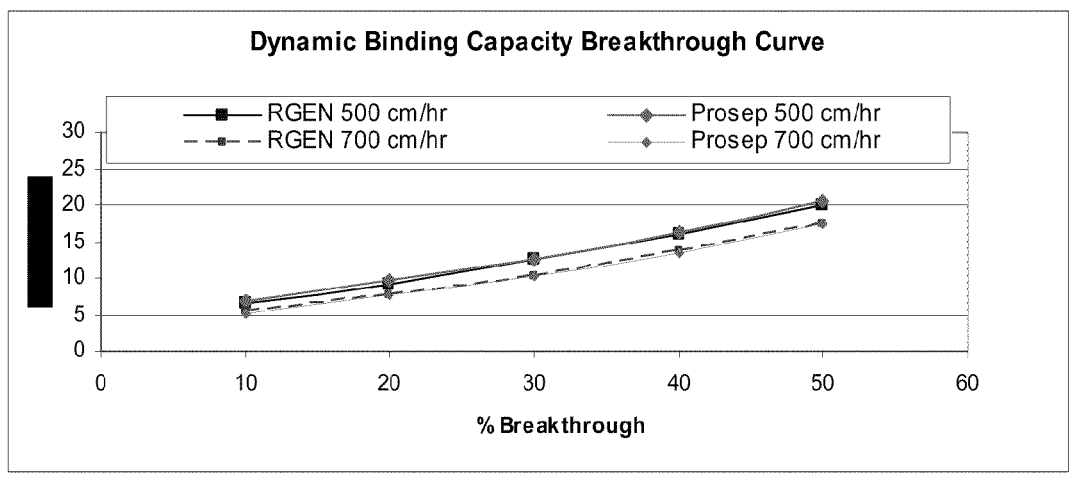

SDS-PAGE results were consistent with the predicted molecular mass of 47 kDA for recombinant truncated rSPA encoded by PA/pREV (FIG. 8). The results indicate that the constructs described herein can be abundantly expressed in *E. coli* without substantial degradation.

Example 3
Functional Characterization of Truncated rSPA Recovered from *E. coli*

Truncated rSPA (SEQ ID NO: 7) was attached to a controlled glass pore resin (CPG-PA) and its functional characteristics were evaluated in a number of tests. To make the rSPA resin, truncated rSPA (from clone 18a in Example 2) was harvested and purified. Truncated rSPA was fused to control pore glass beads and functional characteristics were compared to those of Millipore's PROSEP® A High Capacity protein A controlled pore glass resin (Catalog No. 113115824).

Static Binding Assay

A static polyclonal binding assay was performed by equilibrating resin with phosphate buffered saline (PBS) buffer pH 7.2. Polyclonal human IgG (hIgG) was added and allowed to incubate at room temperature for 30 minutes with end over end mixing. The resin was washed with PBS buffer pH 7.2. The hIgG protein was eluted with 0.2 M Glycine pH 2.0. The amount of hIgG in the eluate was determined by measuring UV absorbance at 280 nm, and the binding capacity calculated. The assay was performed three consecutive times, using the same glass-bound protein A samples to determine the persistent binding capacity of each product after repeated use.

Results of the static binding assay indicate that CPG-rSPA has a similar static binding capacity to that of the PROSEP® A product. Binding capacity was determined to be 36.9+0.2 mg IgG per ml of CPG-rSPA resin compared to 35.2+0.4 mg IgG per ml resin of PROSEP® A product in the first cycle. The results in Table 2 indicate that after three consecutive binding experiments, neither product suffered significant reduction of binding capacity.

TABLE 2

| Sample | Result (mg IgG/ml resin) | | |
|---|---|---|---|
| | Cycle 1 | Cycle 2 | Cycle 3 |
| CPG-rSPA | 36.9 ± 0.2 | 36.2 ± 0.4 | 36.0 ± 0.6 |
| PROSEP A | 35.2 ± 0.4 | 35.4 ± 1.2 | 34.7 ± 1.0 |

Protein A Leaching

A protein A ELISA kit (from Repligen) was used to quantify the amount of protein A that leached into the eluates used to determine the static binding capacity shown in Table 2. ELISAs were performed as indicated by the manufacturer.

Results in Table 3 indicate that less protein A leached into the first cycle eluate from CPG-rSPA than from the PROSEP® A product. In second and third cycles, protein A leaching was comparable for both protein A resins.

TABLE 3

| Sample | Result (ng PA/mg hIgG) | | |
|---|---|---|---|
| | Cycle 1 | Cycle 2 | Cycle 3 |
| CPG-rSPA | 14.1 ± 3.8 | 10 ± 1.1 | 11.4 ± 4.7 |
| PROSEP A | 31.9 ± 8.4 | 16.3 ± 2.1 | 10.1 ± 1.4 |

Capacity Following Cleaning and Regeneration Exposure Cycles

Binding capacity for CPG-rSPA and PROSEP A resins were evaluated subsequent to regeneration and cleaning. Resins were washed with 0.3% HCl pH 1.5 and then exposed for 1 hour to 6 M Guanidine. Guanidine was removed by washing resins with 0.3% HCl pH 1.5, followed by an incubation period of 1 hour in the HCL solution. Following cleaning, each resin was equilibrated with PBS and the static hIgG binding capacity was measured as described above in section 1 (Static Binding Assay).

Results in Table 4 show no meaningful decrease in the binding capacity of the CPG-rSPA following three repeated cycles of HCL and Guanidine exposure consistent with PROSEP® A HC results.

TABLE 4

| Sample | Result (mg IgG/ml resin) | | | |
|---|---|---|---|---|
| | Pre-clean | Cycle 1 | Cycle 2 | Cycle 3 |
| CPG-rSPA | 35.2 ± 0.2 | 35.1 ± 0.2 | 32.9 ± 1.0 | 33.3 ± 0.8 |
| PROSEP A | 34.8 ± 1.2 | 31.9 ± 0.4 | 35.4 ± 2.52 | 34.6 ± 0.8 |

Non-Specific Protein Adsorption Following Cleaning and Regeneration

Each resin was incubated with Chinese Hamster Ovary (CHO) K1 cell conditioned medium containing 5% FBS at room temperature for 30 minutes. The resin was washed with PBS and then eluted with glycine pH 2.0 and neutralized with Tris buffer. Eluates were analyzed by (i) SDS-PAGE and silver staining the protein gels and (ii) a CHO host Protein ELISA (Cygnus Technologies).

SDS-PAGE showed several non-specific protein bands for both CPG-rSPA and the PROSEP® A HC that were similar in molecular weight and intensity (Data not shown). ELISA assay was not able to quantify bound host CHO proteins, indicating that both resins bind less than less than 5 ng CHO Protein/mg hIgG, the limit of detection for the assay.

Dynamic Binding Capacity

Dynamic binding breakthrough curves were generated by subjecting CPG-rSPA and PROSEP A to flow velocities of 100, 300, 500, and 700 cm/hr. A feed stream of 1.0 mg/ml polyclonal human IgG was used with a resin volume of 0.5 ml and a column bed height of 2.5 cm. Capacity is reported at 10% breakthrough.

Under the conditions tested, CPG-PA performed comparably to PROSEP® A HC at each flow velocity. See Table 5 and FIG. 10.

TABLE 5

| | Capacity at 10% BT (mg IgG/ml resin) | | | |
|---|---|---|---|---|
| Sample | 100 cm/hr | 300 cm/hr | 500 cm/hr | 700 cm/hr |
| CPG-rSPA | 19.5 | 6.2 | 6.4 | 5.3 |
| PROSEP A | 20 | 6.9 | 6.9 | 5.3 |

The results of the functional comparative analysis described herein indicate that recombinant truncated rSPA expressed in *E. coli*, when attached to a controlled pore glass resin, performed at least as well and, in some cases better, than Millipore's PROSEP A product, which incorporates an SPA ligand derived from native *S. aureus*.

Example 4

Functional Advantage of a Truncated X Domain

This example demonstrates the advantage of rSPA containing a truncated X domain compared to rSPA without an X domain on chromatography resin immunoglobulin binding capacities. rSPA and a Protein A (TPA), which contains the five Immunoglobulin binding domains, but does not contain any of the X domain, were immobilized onto SEPHAROSE™ 4 Fast Flow resin (Amersham). The protein immobilizations were performed using equivalent molar concentrations of each protein A under identical conditions. A static polyclonal human IgG (hIgG) binding assay was performed as previously described. The rSPA immobilized product had a 14 to 22% greater hIgG capacity than the X domain deficient TPA (see Table 6).

TABLE 6

| Sample | Protein A Concentration [uM] | Static hIgG Binding Capacity [g/L] |
|---|---|---|
| TPA | 50 | 15.5 + 0.5 |
| rSPA | 50 | 18.8 + 0.7 |
| TPA | 200 | 41.4 + 1.7 |
| rSPA | 200 | 47.2 + 1.1 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule comprising a nucleic acid sequence encoding a polypeptide consisting of SEQ ID NO:5.

2. The isolated nucleic acid molecule of claim 1, wherein the coding sequence is codon-optimized for expression in a non-pathogenic organism.

3. The isolated nucleic acid molecule of claim 1, wherein the sequence encoding the polypeptide is operably linked to an expression control sequence.

4. The isolated nucleic acid molecule of claim 1, wherein the sequence encoding the polypeptide is operably linked to a bacterial ribosome binding site.

5. The isolated nucleic acid molecule of claim 4, wherein the ribosome binding site is

```
ACGCGTGGAGGATGATTAA         (SEQ ID NO:3).
```

6. An expression vector comprising the nucleic acid molecule of claim 1 operably linked to an expression control sequence.

7. A bacterial cell comprising the vector of claim 6.

8. A bacterial cell comprising the nucleic acid of claim 1 operably linked to an expression control sequence.

9. A bacterial cell transformed with the vector of claim 6, or a progeny of the cell, wherein the cell expresses a truncated protein A polypeptide consisting of SEQ ID NO:5.

10. The bacterial cell of claim 7, wherein the cell is a non-pathogenic bacterial cell.

11. The bacterial cell of claim 7, wherein the cell is an *Escherichia coli* cell.

12. An *Escherichia coli* cell comprising an exogenous nucleic acid molecule that encodes a polypeptide consisting of SEQ ID NO:5.

13. An *Escherichia coli* cell comprising an exogenous nucleic acid molecule that encodes a polypeptide consisting of SEQ ID NO:7.

14. The cell of claim 13, wherein the coding sequence is codon-optimized for expression in *Escherichia coli*.

15. A method of producing a truncated protein A polypeptide consisting of SEQ ID NO:5, the method comprising culturing the cell of claim 7 under conditions permitting expression of the polypeptide.

16. The method of claim 15, further comprising purifying the truncated protein A polypeptide from the cytoplasm of the cell.

17. A method of producing affinity chromatography resin comprising a truncated protein A polypeptide consisting of SEQ ID NO:5, said method comprising performing the method of claim 16 and immobilizing the truncated protein A polypeptide on a solid support material.

18. The method of claim 17, wherein the solid support material is selected from the group consisting of cellulose, agarose, nylon, and silica.

19. The method of claim 17 wherein the solid support material is a porous bead or a coated particle.

20. The method of claim 17, wherein the solid support material is a controlled pore glass.

21. A method of purifying a protein comprising an Fc region of an IgG immunoglobulin, the method comprising
  contacting the affinity chromatography resin comprising a polypeptide consisting of SEQ ID NO:5 made according to claim 17 with a solution comprising a protein comprising an Fc region of an IgG immunoglobulin; washing the substrate; and
  eluting bound protein comprising an Fc region of an IgG immunoglobulin.

* * * * *

SEQUENCE LISTING

```
<160> NUMBER OF SEQ ID NOS: 24

<210> SEQ ID NO 1
<211> LENGTH: 1272
<212> TYPE: DNA
<213> ORGANISM: Artificial Sequence
<220> FEATURE:
<223> OTHER INFORMATION: Synthetically generated oligonucleotide

<400> SEQUENCE: 1
atggcgcaac acgatgaagc tcaacagaac gctttttacc aggtactgaa catgccgaac      60
ctgaacgcgg atcagcgcaa cggtttcatc cagagcctga aagacgaccc ttctcagtcc     120
gcaaacgttc tgggcgaggc tcagaaactg aacgacagcc aggccccaaa agcagatgct     180
cagcaaaata acttcaacaa ggaccagcag agcgcattct acgaaatcct gaacatgcca     240
aatctgaacg aagctcaacg caacggcttc attcagtctc tgaaagacga tccgtcccag     300
tccactaacg ttctgggtga agctaagaag ctgaacgaat cccaggcacc aaaagcagac     360
aacaacttca acaaagagca gcagaacgct ttctatgaaa tcttgaacat gcctaacctg     420
aatgaagaac agcgtaacgg cttcatccag tctctgaagg acgaccctag ccagtctgct     480
aacctgctgt ccgaagcaaa aaaactgaac gagtcccagg ctccaaaagc ggataacaaa     540
ttcaacaagg agcagcagaa cgcattctac gaaatcctgc acctgccgaa cctgaacgaa     600
gaacagcgta acggtttcat ccaatccctg aaagacgatc cttcccagtc cgcaaatctg     660
ctggcagaag caaagaaact gaacgacgca caggcaccga aggctgacaa caagttcaac     720
aaagagcagc agaatgcctt ctacgagatt ctgcatctgc caaacctgac tgaggagcag     780
cgcaacggtt tcattcagtc cctgaaggac gacccaagcg tcagcaagga aatcctggct     840
gaggcgaaaa aactgaacga tgcacaggct ccgaaggaag aagacaacaa taaacctggt     900
aaagaagata ataataagcc tggcaaggaa gataacaaca agccgggcaa ggaggacaac     960
```

| | |
|---|---:|
| aataaaccgg gcaaagagga taataacaag cctggtaagg aagacaacaa caaaccaggc | 1020 |
| aaagaagatg gcaacaagcc gggtaaggag gataataaaa aaccaggcaa ggaagacggc | 1080 |
| aacaaacctg gcaaggagga taacaaaaag ccaggcaagg aggatggtaa taaaccgggc | 1140 |
| aaagaagacg gcaacaagcc tggtaaagaa gacggtaacg gtgtacacgt cgttaaacct | 1200 |
| ggtgacaccg tgaacgacat cgctaaggct aatggcacca cggcagacaa gattgcagcg | 1260 |
| gacaataaat aa | 1272 |

<210> SEQ ID NO 2
<211> LENGTH: 1523
<212> TYPE: DNA
<213> ORGANISM: Artificial Sequence
<220> FEATURE:
<223> OTHER INFORMATION: Synthetically generated oligonucleotide

<400> SEQUENCE: 2

| | |
|---|---:|
| atggcgcaac acgatgaagc tcaccagaac gcttttttacc aggtactgaa catgccgaac | 60 |
| ctgaacgcgg atcagcgcaa cggtttcatc cagagcctga agacgacccc ttctcagtcc | 120 |
| gcaaacgttc tgggcgaggc tcagaaactg aacgacagcc aggccccaaa agcagatgct | 180 |
| cagcaaaata acttcaacaa ggaccagcag agcgcattct acgaaatcct gaacatgcca | 240 |
| aatctgaacg aagctcaacg caacggcttc attcagtctc tgaaagacga tccgtcccag | 300 |
| tccactaacg ttctgggtga agctaagaag ctgaacgaat cccaggcacc aaaagcagac | 360 |
| aacaacttca acaaagagca gcagaacgct ttctatgaaa tcttgaacat gcctaacctg | 420 |
| aatgaagaac agcgtaacgg cttcatccag tctctgaagg acgaccctag ccagtctgct | 480 |
| aacctgctgt ccgaagcaaa aaaactgaac gagtcccagg ctccaaaagc ggataacaaa | 540 |
| ttcaacaagg agcagcagaa cgcattctac gaaatcctgc acctgccgaa cctgaacgaa | 600 |
| gaacagcgta acggtttcat ccaatccctg aaagacgatc cttcccagtc cgcaaatctg | 660 |
| ctggcagaag caaagaaact gaacgacgca caggcaccga aggctgacaa caagttcaac | 720 |
| aaagagcagc agaatgcctt ctacgagatt ctgcatctgc caaacctgac tgaggagcag | 780 |
| cgcaacggtt tcattcagtc cctgaaggac gacccaagcg tcagcaagga aatcctggct | 840 |
| gaggcgaaaa aactgaacga tgcacaggct ccgaaggaag aagacaacaa taaacctggt | 900 |
| aaagaagata ataataagcc tggcaaggaa gataacaaca agccgggcaa ggaggacaac | 960 |
| aataaaccgg gcaaagagga taataacaag cctggtaagg aagacaacaa caaaccaggc | 1020 |
| aaagaagatg gcaacaagcc gggtaaggag gataataaaa aaccaggcaa ggaagacggc | 1080 |
| aacaaacctg gcaaggagga taacaaaaag ccaggcaagg aggatggtaa taaaccgggc | 1140 |
| aaagaagacg gcaacaagcc tggtaaagaa gacggtaacg gtgtacacgt cgttaaacct | 1200 |
| ggtgacaccg tgaacgacat cgctaaggct aatggcacca cggcagacaa gattgcagcg | 1260 |
| gacaataaat agctgataa ataaggatcc ggatccgtcg acaagcttcc cgggagctcg | 1320 |
| aattcttgaa gacgaaaggg cctcgtgata cgcctatttt tataggttaa tgtcatgata | 1380 |
| ataatggttt cttagacgtc ggtaccagcc cgcctaatga gcgggctttt ttttgacgtc | 1440 |
| aggtggcact tttcggggaa atgtgcgcgg aaccctatt tgtttatttt tctaaataca | 1500 |
| gaggaagaca acaacaagcc tgg | 1523 |

<210> SEQ ID NO 3
<211> LENGTH: 19
<212> TYPE: DNA
<213> ORGANISM: Artificial Sequence

```
<220> FEATURE:
<223> OTHER INFORMATION: A bacterial ribosome binding site

<400> SEQUENCE: 3
acgcgtggag gatgattaa                                                        19

<210> SEQ ID NO 4
<211> LENGTH: 524
<212> TYPE: PRT
<213> ORGANISM: Staphylococcus aureus

<400> SEQUENCE: 4

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
                325                 330                 335

Glu Asp Asn Asn Lys Pro Gly Lys Glu Asp Asn Asn Lys Pro Gly Lys
```

```
                        340                 345                 350
Glu Asp Asn Asn Lys Pro Gly Lys Glu Asp Asn Asn Lys Pro Gly Lys
                355                 360                 365

Glu Asp Asn Asn Lys Pro Gly Lys Glu Asp Gly Asn Lys Pro Gly Lys
            370                 375                 380

Glu Asp Asn Lys Lys Pro Gly Lys Glu Asp Gly Asn Lys Pro Gly Lys
385                 390                 395                 400

Glu Asp Asn Lys Lys Pro Gly Lys Glu Asp Gly Asn Lys Pro Gly Lys
                405                 410                 415

Glu Asp Gly Asn Lys Pro Gly Lys Glu Asp Gly Asn Gly Val His Val
            420                 425                 430

Val Lys Pro Gly Asp Thr Val Asn Asp Ile Ala Lys Ala Asn Gly Thr
        435                 440                 445

Thr Ala Asp Lys Ile Ala Ala Asp Asn Lys Leu Ala Asp Lys Asn Met
    450                 455                 460

Ile Lys Pro Gly Gln Glu Leu Val Val Asp Lys Lys Gln Pro Ala Asn
465                 470                 475                 480

His Ala Asp Ala Asn Lys Ala Gln Ala Leu Pro Glu Thr Gly Glu Glu
                485                 490                 495

Asn Pro Phe Ile Gly Thr Thr Val Phe Gly Gly Leu Ser Leu Ala Leu
            500                 505                 510

Gly Ala Ala Leu Leu Ala Gly Arg Arg Arg Glu Leu
        515                 520

<210> SEQ ID NO 5
<211> LENGTH: 422
<212> TYPE: PRT
<213> ORGANISM: Artificial Sequence
<220> FEATURE:
<223> OTHER INFORMATION: Synthetically generated peptide

<400> SEQUENCE: 5

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp Gln Gln Ser Ala Phe Tyr Glu Ile Leu Asn Met Pro Asn
65                  70                  75                  80

Leu Asn Glu Ala Gln Arg Asn Gly Phe Ile Gln Ser Leu Lys Asp Asp
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Gln Gln Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Asp Asp Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Gln Gln Asn Ala Phe Tyr Glu Ile Leu
```

```
                180                 185                 190
His Leu Pro Asn Leu Asn Glu Glu Gln Arg Asn Gly Phe Ile Gln Ser
        195                 200                 205

Leu Lys Asp Asp Pro Ser Gln Ser Ala Asn Leu Leu Ala Glu Ala Lys
        210                 215                 220

Lys Leu Asn Asp Ala Gln Ala Pro Lys Ala Asp Asn Lys Phe Asn Lys
225                 230                 235                 240

Glu Gln Gln Asn Ala Phe Tyr Glu Ile Leu His Leu Pro Asn Leu Thr
                245                 250                 255

Glu Glu Gln Arg Asn Gly Phe Ile Gln Ser Leu Lys Asp Asp Pro Ser
        260                 265                 270

Val Ser Lys Glu Ile Leu Ala Glu Ala Lys Lys Leu Asn Asp Ala Gln
        275                 280                 285

Ala Pro Lys Glu Glu Asp Asn Asn Lys Pro Gly Lys Glu Asp Asn Asn
        290                 295                 300

Lys Pro Gly Lys Glu Asp Asn Asn Lys Pro Gly Lys Glu Asp Asn Asn
305                 310                 315                 320

Lys Pro Gly Lys Glu Asp Asn Asn Lys Pro Gly Lys Glu Asp Asn Asn
                325                 330                 335

Lys Pro Gly Lys Glu Asp Gly Asn Lys Pro Gly Lys Glu Asp Asn Lys
                340                 345                 350

Lys Pro Gly Lys Glu Asp Gly Asn Lys Pro Gly Lys Glu Asp Asn Lys
        355                 360                 365

Lys Pro Gly Lys Glu Asp Gly Asn Lys Pro Gly Lys Glu Asp Gly Asn
        370                 375                 380

Lys Pro Gly Lys Glu Asp Gly Asn Gly Val His Val Val Lys Pro Gly
385                 390                 395                 400

Asp Thr Val Asn Asp Ile Ala Lys Ala Asn Gly Thr Thr Ala Asp Lys
                405                 410                 415

Ile Ala Ala Asp Asn Lys
            420

<210> SEQ ID NO 6
<211> LENGTH: 458
<212> TYPE: PRT
<213> ORGANISM: Artificial Sequence
<220> FEATURE:
<223> OTHER INFORMATION: Synthetically generated peptide

<400> SEQUENCE: 6

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Thr Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
```

-continued

```
                 115                 120                 125
Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
                325                 330                 335

Glu Asp Asn Asn Lys Pro Gly Lys Glu Asp Asn Asn Lys Pro Gly Lys
            340                 345                 350

Glu Asp Asn Asn Lys Pro Gly Lys Glu Asp Asn Asn Lys Pro Gly Lys
        355                 360                 365

Glu Asp Asn Asn Lys Pro Gly Lys Glu Asp Gly Asn Lys Pro Gly Lys
    370                 375                 380

Glu Asp Asn Lys Lys Pro Gly Lys Glu Asp Gly Asn Lys Pro Gly Lys
385                 390                 395                 400

Glu Asp Asn Lys Lys Pro Gly Lys Glu Asp Gly Asn Lys Pro Gly Lys
                405                 410                 415

Glu Asp Gly Asn Lys Pro Gly Lys Glu Asp Gly Asn Gly Val His Val
            420                 425                 430

Val Lys Pro Gly Asp Thr Val Asn Asp Ile Ala Lys Ala Asn Gly Thr
        435                 440                 445

Thr Ala Asp Lys Ile Ala Ala Asp Asn Lys
    450                 455

<210> SEQ ID NO 7
<211> LENGTH: 426
<212> TYPE: PRT
<213> ORGANISM: Artificial Sequence
<220> FEATURE:
<223> OTHER INFORMATION: Synthetically generated peptide

<400> SEQUENCE: 7

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
```

```
                20                  25                  30
Lys Asp Asp Pro Ser Gln Ser Ala Asn Val Leu Gly Glu Ala Gln Lys
            35                  40                  45

Leu Asn Asp Ser Gln Ala Pro Lys Ala Asp Ala Gln Gln Asn Asn Phe
        50                  55                  60

Asn Lys Asp Gln Gln Ser Ala Phe Tyr Glu Ile Leu Asn Met Pro Asn
 65                  70                  75                  80

Leu Asn Glu Ala Gln Arg Asn Gly Phe Ile Gln Ser Leu Lys Asp Asp
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Gln Gln Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Asp Asp Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Gln Gln Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Asp Asp Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Gln Gln Asn Ala Phe Tyr Glu Ile Leu His Leu Pro Asn Leu Thr
                245                 250                 255

Glu Glu Gln Arg Asn Gly Phe Ile Gln Ser Leu Lys Asp Asp Pro Ser
            260                 265                 270

Val Ser Lys Glu Ile Leu Ala Glu Ala Lys Lys Leu Asn Asp Ala Gln
        275                 280                 285

Ala Pro Lys Glu Glu Asp Asn Asn Lys Pro Gly Lys Glu Asp Asn Asn
    290                 295                 300

Lys Pro Gly Lys Glu Asp Asn Asn Lys Pro Gly Lys Glu Asp Asn Asn
305                 310                 315                 320

Lys Pro Gly Lys Glu Asp Asn Asn Lys Pro Gly Lys Glu Asp Asn Asn
                325                 330                 335

Lys Pro Gly Lys Glu Asp Gly Asn Lys Pro Gly Lys Glu Asp Asn Lys
            340                 345                 350

Lys Pro Gly Lys Glu Asp Gly Asn Lys Pro Gly Lys Glu Asp Asn Lys
        355                 360                 365

Lys Pro Gly Lys Glu Asp Gly Asn Lys Pro Gly Lys Glu Asp Gly Asn
    370                 375                 380

Lys Pro Gly Lys Glu Asp Gly Asn Gly Val His Val Val Lys Pro Gly
385                 390                 395                 400

Asp Thr Val Asn Asp Ile Ala Lys Ala Asn Gly Thr Thr Ala Asp Lys
                405                 410                 415

Ile Ala Ala Asp Asn Lys Leu Ala Asp Lys
            420                 425

<210> SEQ ID NO 8
```

```
<211> LENGTH: 8
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 7, 8
<223> OTHER INFORMATION: Xaa = any amino acid

<400> SEQUENCE: 8

Lys Pro Gly Lys Glu Asp Xaa Xaa
 1               5

<210> SEQ ID NO 9
<211> LENGTH: 56
<212> TYPE: PRT
<213> ORGANISM: Artificial Sequence
<220> FEATURE:
<223> OTHER INFORMATION: Synthetically generated peptide

<400> SEQUENCE: 9

Ala Gln His Asp Glu Ala Gln Gln Asn Ala Phe Tyr Gln Val Leu Asn
 1               5                  10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys
    50                  55

<210> SEQ ID NO 10
<211> LENGTH: 61
<212> TYPE: PRT
<213> ORGANISM: Artificial Sequence
<220> FEATURE:
<223> OTHER INFORMATION: Synthetically generated peptide

<400> SEQUENCE: 10

Ala Asp Ala Gln Gln Asn Asn Phe Asn Lys Asp Gln Gln Ser Ala Phe
 1               5                  10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 11
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 11

Ala Asp Asn Asn Phe Asn Lys Glu Gln Gln Asn Ala Phe Tyr Glu Ile
 1               5                  10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55
```

<210> SEQ ID NO 12
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 12

```
Ala Asp Asn Lys Phe Asn Lys Glu Gln Gln Asn Ala Phe Tyr Glu Ile
 1               5                  10                  15
Leu His Leu Pro Asn Leu Asn Glu Glu Gln Arg Asn Gly Phe Ile Gln
            20                  25                  30
Ser Leu Lys Asp Asp Pro Ser Gln Ser Ala Asn Leu Leu Ala Glu Ala
        35                  40                  45
Lys Lys Leu Asn Asp Ala Gln Ala Pro Lys
    50                  55
```

<210> SEQ ID NO 13
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 13

```
Ala Asp Asn Lys Phe Asn Lys Glu Gln Gln Asn Ala Phe Tyr Glu Ile
 1               5                  10                  15
Leu His Leu Pro Asn Leu Thr Glu Glu Gln Arg Asn Gly Phe Ile Gln
            20                  25                  30
Ser Leu Lys Asp Asp Pro Ser Val Ser Lys Glu Ile Leu Ala Glu Ala
        35                  40                  45
Lys Lys Leu Asn Asp Ala Gln Ala Pro Lys
    50                  55
```

<210> SEQ ID NO 14
<211> LENGTH: 180
<212> TYPE: PRT
<213> ORGANISM: Artificial Sequence
<220> FEATURE:
<223> OTHER INFORMATION: Synthetically generated peptide

<400> SEQUENCE: 14

```
Glu Glu Asp Asn Asn Lys Pro Gly Lys Glu Asp Asn Asn Lys Pro Gly
 1               5                  10                  15
Lys Glu Asp Asn Asn Lys Pro Gly Lys Glu Asp Asn Asn Lys Pro Gly
            20                  25                  30
Lys Glu Asp Asn Asn Lys Pro Gly Lys Glu Asp Asn Asn Lys Pro Gly
        35                  40                  45
Lys Glu Asp Gly Asn Lys Pro Gly Lys Glu Asp Asn Lys Lys Pro Gly
    50                  55                  60
Lys Glu Asp Gly Asn Lys Pro Gly Lys Glu Asp Asn Lys Lys Pro Gly
65                  70                  75                  80
Lys Glu Asp Gly Asn Lys Pro Gly Lys Glu Asp Gly Asn Lys Pro Gly
                85                  90                  95
Lys Glu Asp Gly Asn Gly Val His Val Val Lys Pro Gly Asp Thr Val
            100                 105                 110
Asn Asp Ile Ala Lys Ala Asn Gly Thr Thr Ala Asp Lys Ile Ala Ala
        115                 120                 125
```

```
Asp Asn Lys Leu Ala Asp Lys Asn Met Ile Lys Pro Gly Gln Glu Leu
    130                 135                 140
Val Val Asp Lys Lys Gln Pro Ala Asn His Ala Asp Ala Asn Lys Ala
145                 150                 155                 160
Gln Ala Leu Pro Glu Thr Gly Glu Glu Asn Pro Phe Ile Gly Thr Thr
                165                 170                 175
Val Phe Gly Gly
            180

<210> SEQ ID NO 15
<211> LENGTH: 131
<212> TYPE: PRT
<213> ORGANISM: Artificial Sequence
<220> FEATURE:
<223> OTHER INFORMATION: Synthetically generated peptide

<400> SEQUENCE: 15

Glu Glu Asp Asn Asn Lys Pro Gly Lys Glu Asp Asn Asn Lys Pro Gly
  1               5                  10                  15
Lys Glu Asp Asn Asn Lys Pro Gly Lys Glu Asp Asn Asn Lys Pro Gly
             20                  25                  30
Lys Glu Asp Asn Asn Lys Pro Gly Lys Glu Asp Asn Asn Lys Pro Gly
         35                  40                  45
Lys Glu Asp Gly Asn Lys Pro Gly Lys Glu Asp Asn Lys Lys Pro Gly
     50                  55                  60
Lys Glu Asp Gly Asn Lys Pro Gly Lys Glu Asp Asn Lys Lys Pro Gly
 65                  70                  75                  80
Lys Glu Asp Gly Asn Lys Pro Gly Lys Glu Asp Gly Asn Lys Pro Gly
                 85                  90                  95
Lys Glu Asp Gly Asn Gly Val His Val Val Lys Pro Gly Asp Thr Val
                100                 105                 110
Asn Asp Ile Ala Lys Ala Asn Gly Thr Thr Ala Asp Lys Ile Ala Ala
            115                 120                 125
Asp Asn Lys
    130

<210> SEQ ID NO 16
<211> LENGTH: 2270
<212> TYPE: DNA
<213> ORGANISM: Artificial Sequence
<220> FEATURE:
<223> OTHER INFORMATION: A partial nucleotide
      sequence of an E. coli expression vector.

<400> SEQUENCE: 16
gcagcggtcg ggctgaacgg ggggttcgtg cacacagccc agcttggagc gaacgaccta    60
caccgaactg agatacctac agcgtgagct atgagaaagc gccacgcttc ccgaagggag   120
aaaggcggac aggtatccgg taagcggcag ggtcggaaca ggagagcgca cgagggagct   180
tccaggggga aacgcctggt atctttatag tcctgtcggg tttcgccacc tctgacttga   240
gcgtcgattt ttgtgatgct cgtcaggggg gcggagccta tggaaaaacg ccagcaacgc   300 ggcctttta cggttcctgg ccttttgctg ccttttgct cacatgttct ttcctgcgtt   360
atcccctgat tctgtggata accgtattac cgcctttgag tgagctgata ccgctcgccg   420
cagccgaacg accgagcgca gcgagtcagt gagcgaggaa gcggaagagc gcctgatgcg   480
gtattttctc cttacgcatc tgtgcggtat ttcacaccgc atatgtcatg agagtttatc   540
```

```
gttcccaata cgctcgaacg aacgttcggt tgcttatttt atggcttctg tcaacgctgt    600
tttaaagatt aatgcgatct atatcacgct gtgggtattg cagttttttgg tttttttgatc  660 gcggtgtcag ttcttttttat ttccatttct cttccatggg tttctcacag ataactgtgt   720
gcaacacaga attggttcga acgcgtggag gatgattaaa tggcgcaaca cgatgaagct   780
caacagaacg cttttttacca ggtactgaac atgccgaacc tgaacgcgga tcagcgcaac   840
ggtttcatcc agagcctgaa agacgaccct tctcagtccg caaacgttct gggcgaggct   900
cagaaactga cgacagcca ggccccaaaa gcagatgctc agcaaaataa cttcaacaag   960
gaccagcaga gcgcattcta cgaaatcctg aacatgccaa atctgaacga agctcaacgc  1020
aacggcttca ttcagtctct gaaagacgat ccgtcccagt ccactaacgt tctgggtgaa  1080
gctaagaagc tgaacgaatc ccaggcacca aaagcagaca caacttcaa caaagagcag  1140 cagaacgctt tctatgaaat cttgaacatg cctaacctga tgaagaaca gcgtaacggc  1200 ttcatccagt ctctgaagga cgaccctagc cagtctgcta acctgctgtc cgaagcaaaa  1260
aaactgaacg agtcccaggc tccaaaagcg ataacaaat tcaacaagga gcagcagaac  1320
gcattctacg aaatcctgca cctgccgaac ctgaacgaag aacagcgtaa cggtttcatc  1380
caatccctga agacgatcc ttcccagtcc gcaaatctgc tggcagaagc aaagaaactg  1440
aacgacgcac aggcaccgaa ggctgacaac aagttcaaca aagagcagca gaatgccttc  1500
tacgagattc tgcatctgcc aaacctgact gaggagcagc gcaacggttt cattcagtcc  1560
ctgaaggacg acccaagcgt cagcaaggaa atcctggctg aggcgaaaaa actgaacgat  1620
gcacaggctc cgaaggaaga agacaacaat aaacctggta agaagataa taataagcct  1680 ggcaaggaag ataacaacaa gccgggcaag gaggacaaca ataaaccggg caaagaggat  1740
aataacaagc tggtaagga agacaacaac aaaccaggca agaagatgg caacaagccg  1800 ggtaaggagg ataataaaaa accaggcaag gaagacggca caaacctgg caaggaggat  1860 aacaaaaagc caggcaagga ggatggtaat aaaccgggca agaagacgg caacaagcct  1920 ggtaaagaag acggtaacgg tgtacacgtc gttaaacctg gtgacaccgt gaacgacatc  1980
gctaaggcta atggcaccac ggcagacaag attgcagcgg acaataaata aggatccgga  2040
tccgtcgaca agcttcccgg gagctcgaat tcttgaagac gaaagggcct cgtgatacgc  2100
ctatttttat aggttaatgt catgataata atggtttctt agacgtcggt accagcccgc  2160
ctaatgagcg ggcttttttt tgacgtcagg tggcactttt cggggaaatg tgcgcggaac  2220
ccctatttgt ttatttttct aaatacagag gaagacaaca acaagcctgg                2270
```

<210> SEQ ID NO 17
<211> LENGTH: 471
<212> TYPE: PRT
<213> ORGANISM: Artificial Sequence
<220> FEATURE:
<223> OTHER INFORMATION: Synthetically generated peptide

<400> SEQUENCE: 17

Ala Gln His Asp Glu Ala Gln Gln Asn Ala Phe Tyr Gln Val Leu Asn
 1               5                  10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

```
Asn Lys Asp Gln Gln Ser Ala Phe Tyr Glu Ile Leu Asn Met Pro Asn
 65                  70                  75                  80

Leu Asn Glu Ala Gln Arg Asn Gly Phe Ile Gln Ser Leu Lys Asp Asp
                 85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Gln Gln Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Asp Asp Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Gln Gln Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Asp Asp Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Gln Gln Asn Ala Phe Tyr Glu Ile Leu His Leu Pro Asn Leu Thr
                245                 250                 255

Glu Glu Gln Arg Asn Gly Phe Ile Gln Ser Leu Lys Asp Asp Pro Ser
            260                 265                 270

Val Ser Lys Glu Ile Leu Ala Glu Ala Lys Lys Leu Asn Asp Ala Gln
        275                 280                 285

Ala Pro Lys Glu Glu Asp Asn Asn Lys Pro Gly Lys Glu Asp Asn Asn
    290                 295                 300

Lys Pro Gly Lys Glu Asp Asn Asn Lys Pro Gly Lys Glu Asp Asn Asn
305                 310                 315                 320

Lys Pro Gly Lys Glu Asp Asn Asn Lys Pro Gly Lys Glu Asp Asn Asn
                325                 330                 335

Lys Pro Gly Lys Glu Asp Gly Asn Lys Pro Gly Lys Glu Asp Asn Lys
            340                 345                 350

Lys Pro Gly Lys Glu Asp Gly Asn Lys Pro Gly Lys Glu Asp Asn Lys
        355                 360                 365

Lys Pro Gly Lys Glu Asp Gly Asn Lys Pro Gly Lys Glu Asp Gly Asn
    370                 375                 380

Lys Pro Gly Lys Glu Asp Gly Asn Gly Val His Val Val Lys Pro Gly
385                 390                 395                 400

Asp Thr Val Asn Asp Ile Ala Lys Ala Asn Gly Thr Thr Ala Asp Lys
                405                 410                 415

Ile Ala Ala Asp Asn Lys Leu Ala Asp Lys Asn Met Ile Lys Pro Gly
            420                 425                 430

Gln Glu Leu Val Val Asp Lys Lys Gln Pro Ala Asn His Ala Asp Ala
        435                 440                 445

Asn Lys Ala Gln Ala Leu Pro Glu Thr Gly Glu Glu Asn Pro Phe Ile
    450                 455                 460

Gly Thr Thr Val Phe Gly Gly
465                 470
```

```
<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
aaagcagatg ctcagcaa                                                   18

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
gatttccttg ctgacgctt                                                  19

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
aagcgtcagc aaggaaatc                                                  19

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
gatctatatc acgctgtgg                                                  19

<210> SEQ ID NO 22
<211> LENGTH: 1269
<212> TYPE: DNA
<213> ORGANISM: Artificial Sequence
<220> FEATURE:
<223> OTHER INFORMATION: Synthetically generated oligonucleotide

<400> SEQUENCE: 22
atggcgcaac acgatgaagc tcaacaaaat gcttttttatc aagtcttaaa tatgcctaac     60
ttaaatgctg atcaacgcaa tggttttatc caaagcctta aagatgatcc aagccaaagt    120
gctaacgttt taggtgaagc tcaaaaactt aatgactctc aagctccaaa agctgatgcg    180
caacaaaata cttcaacaa agatcaacaa agcgccttct atgaaatctt gaacatgcct    240
aacttaaacg aagcgcaacg taacggcttc attcaaagtc ttaaagacga cccaagccaa    300
agcactaacg ttttaggtga agctaaaaaa ttaaacgaat ctcaagcacc gaaagctgat    360
aacaatttca acaaagaaca acaaaatgct ttctatgaaa tcttgaatat gcctaactta    420
aacgaagaac aacgcaatgg tttcatccaa agcttaaaag atgacccaag ccaaagtgct    480
aacctattgt cagaagctaa aaagttaaat gaatctcaag caccgaaagc ggataacaaa    540
ttcaacaaag aacaacaaaa tgctttctat gaaatcttac atttacctaa cttaaacgaa    600
gaacaacgca atggtttcat ccaaagccta aaagatgacc caagccaaag cgctaacctt    660
```

```
ttagcagaag ctaaaaagct aaatgatgct caagcaccaa agctgacaa caaattcaac      720 aaagaacaac aaaatgcttt ctatgaaatt ttacatttac ctaacttaac tgaagaacaa      780
cgtaacggct tcatccaaag ccttaaagac gatccttcgg tgagcaaaga aattttagca      840
gaagctaaaa agctaaacga tgctcaagca ccaaagagg aagacaataa caagcctggc      900
aaagaagaca ataacaagcc tggcaaagaa gacaataaca agcctggcaa agaagacaac      960
aacaagcctg gcaaagaaga caacaacaag cctggtaaag aagacaacaa caagcctggc     1020
aaagaagacg gcaacaagcc tggtaaagaa gacaacaaaa acctggtaa agaagatggc     1080 aacaagcctg gtaaagaaga caacaaaaaa cctggtaaag aagacggcaa caagcctggc     1140
aaagaagatg gcaacaaacc tggtaaagaa gatggtaacg agtacatgt cgttaaacct     1200 ggtgatacag taaatgacat tgcaaaagca acggcacta ctgctgacaa aattgctgca     1260
gataacaaa                                                             1269

<210> SEQ ID NO 23
<211> LENGTH: 400
<212> TYPE: DNA
<213> ORGANISM: Artificial Sequence
<220> FEATURE:
<223> OTHER INFORMATION: Synthetically generated oligonucleotide

<400> SEQUENCE: 23
tctgtgcggt atttcacacc gcatatgtca tgagagttta tcgttcccaa tacgctcgaa       60
cgaacgttcg gttgcttatt ttatggcttc tgtcaacgct gttttaaaga ttaatgcgat      120
ctatatcacg ctgtgggtat tgcagttttt cgtttttttga tcgcggtgtc agttctttt      180 atttccattt ctcttccatg ggtttctcac agataactgt gtgcaacaca gaattggttc      240
gaacgcgtgg aggatgatta aatggcgcaa cacgatgaag ctcaacagaa cgcttttttac      300 caggtactga acatgccgaa ggacaataaa taaggatccg tcgacaagct tcccgggagc      360
tcgaattctt gaagacgaaa gggcctcgtg atacgcctat                            400

<210> SEQ ID NO 24
<211> LENGTH: 50
<212> TYPE: PRT
<213> ORGANISM: Artificial Sequence
<220> FEATURE:
<223> OTHER INFORMATION: Synthetically generated peptide

<400> SEQUENCE: 24

Glu Arg Val Glu Asp Asp Met Ala Gln His Asp Glu Ala Gln Gln Asn
 1               5                  10                  15

Ala Phe Tyr Gln Val Leu Asn Met Pro Asn Asp Asn Lys Gly Ser Val
            20                  25                  30

Asp Lys Leu Pro Gly Ser Ser Asn Ser Arg Arg Lys Gly Leu Val Ile
        35                  40                  45

Arg Leu
    50
```